(12) United States Patent
Kosinski et al.

(10) Patent No.: US 10,463,798 B2
(45) Date of Patent: *Nov. 5, 2019

(54) FLUSH SYRINGE WITH CONTROLLED PULSATILE FLUSHING

(71) Applicant: Becton, Dickinson and Company, Franklin Lakes, NJ (US)

(72) Inventors: Anthony J. Kosinski, New Providence, NJ (US); Girum Yemane Tekeste, Hackensack, NJ (US); Nichola Charles, Budd Lake, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 10 days.

This patent is subject to a terminal disclaimer.

(21) Appl. No.: 15/864,185

(22) Filed: Jan. 8, 2018

(65) Prior Publication Data

US 2018/0126086 A1 May 10, 2018

Related U.S. Application Data

(63) Continuation of application No. 14/798,648, filed on Jul. 14, 2015, now Pat. No. 9,907,913, which is a
(Continued)

(51) Int. Cl.
*A61M 5/315* (2006.01)
*A61M 5/00* (2006.01)
(Continued)

(52) U.S. Cl.
CPC ...... *A61M 5/31505* (2013.01); *A61M 5/3129* (2013.01); *A61M 5/31501* (2013.01);
(Continued)

(58) Field of Classification Search
CPC ........... A61M 2005/3143; A61M 2005/31508; A61M 2005/3151; A61M 2025/0019;
(Continued)

(56) References Cited

U.S. PATENT DOCUMENTS 3,949,748 A 4/1976 Malmin
4,444,335 A 4/1984 Wood et al.
(Continued)

FOREIGN PATENT DOCUMENTS

CH 518102 A 1/1972
CN 1771066 A 5/2006
(Continued)

OTHER PUBLICATIONS

Final Office Action in U.S. Appl. No. 12/833,551 dated Dec. 26, 2012, 9 pages.
(Continued)

*Primary Examiner* — Rebecca E Eisenberg
(74) *Attorney, Agent, or Firm* — Servilla Whitney LLC

(57) ABSTRACT

Flush syringe assemblies capable of creating pulsatile movement of the plunger rod as it moves in the distal direction within a syringe barrel, while preventing overpressurization of the catheter are provided. An exemplary flush syringe assembly includes a syringe barrel with a first pulsing element and a chamber with flush solution, a plunger rod with a stopper and a second pulsing element that interacts with the first pulsing element to provide an engagement force that causes pulsatile movement of the plunger rod and a thumb press slidably attached to the plunger rod with a pulse control element. The pulse control element is compressible to create a compression force that is greater than the engagement force of the first pulsing element and the second pulsing element.

20 Claims, 21 Drawing Sheets

Related U.S. Application Data continuation of application No. 13/871,682, filed on Apr. 26, 2013, now Pat. No. 9,084,851, which is a continuation of application No. 12/833,551, filed on Jul. 9, 2010, now Pat. No. 8,491,537.

(60) Provisional application No. 61/224,688, filed on Jul. 10, 2009.

(51) Int. Cl.
*A61M 5/31* (2006.01)
*A61M 25/00* (2006.01)

(52) U.S. Cl.
CPC .... *A61M 5/31511* (2013.01); *A61M 5/31595* (2013.01); *A61M 2005/3143* (2013.01); *A61M 2005/3151* (2013.01); *A61M 2005/31508* (2013.01); *A61M 2025/0019* (2013.01); *A61M 2206/10* (2013.01)

(58) Field of Classification Search
CPC .......... A61M 2206/10; A61M 5/31501; A61M 5/31511; A61M 5/31595
See application file for complete search history.

(56) References Cited

U.S. PATENT DOCUMENTS

| | | | |
|---|---|---|---|
| D287,053 S | 12/1986 | Bucchianeri et al. |
| 5,259,840 A | 11/1993 | Boris |
| 5,478,311 A | 12/1995 | Klearman |
| 5,498,243 A | 3/1996 | Vallelunga et al. |
| 5,643,214 A | 7/1997 | Marshall et al. |
| D403,762 S | 1/1999 | Gabbard et al. |
| D420,129 S | 2/2000 | McMahon |
| D432,231 S | 10/2000 | Balestracci |
| D437,050 S | 1/2001 | Balestracci |
| 6,176,846 B1 | 1/2001 | Balestracci |
| D460,820 S | 7/2002 | Niedospial, Jr. |
| 6,419,656 B1 | 7/2002 | Vetter |
| 6,530,906 B2 | 3/2003 | Hu |
| 6,565,529 B1 | 5/2003 | Kimber et al. |
| 6,790,197 B2 | 9/2004 | Kosinski et al. |
| 7,276,049 B2 | 10/2007 | Bang et al. |
| D570,476 S | 6/2008 | Sudo |
| D575,870 S | 8/2008 | Sudo |
| 7,686,784 B2 | 3/2010 | Baik |
| 2002/0007147 A1 | 1/2002 | Capes et al. |
| 2004/0064105 A1 | 4/2004 | Capes et al. |
| 2004/0087910 A1 | 5/2004 | Nemoto |
| 2004/0186427 A1 | 9/2004 | Pok |
| 2004/0199113 A1 | 10/2004 | Capes et al. |
| 2004/0249348 A1 | 12/2004 | Wimpenny et al. |
| 2005/0038385 A1 | 2/2005 | Shen et al. |
| 2005/0065478 A1 | 3/2005 | Alheidt et al. |
| 2005/0148932 A1 | 7/2005 | Rimlinger et al. |
| 2005/0187518 A1 | 8/2005 | Pelkey et al. |
| 2006/0052748 A1 | 3/2006 | Coelho et al. |
| 2006/0111668 A1 | 5/2006 | Baik |
| 2006/0167409 A1 | 7/2006 | Pelkey et al. |
| 2006/0247582 A1 | 11/2006 | Alheidt et al. |
| 2006/0258983 A1 | 11/2006 | Cirac Sole et al. |
| 2007/0005022 A1 | 1/2007 | Byrne et al. |
| 2007/0073225 A1 | 3/2007 | Lee et al. |
| 2007/0078406 A1 | 4/2007 | Lee |
| 2007/0129674 A1 | 6/2007 | Liversidge |
| 2007/0135764 A1 | 6/2007 | Chen |
| 2007/0179452 A1 | 8/2007 | Kosinski |
| 2007/0299395 A1 | 12/2007 | Pelkey et al. |
| 2008/0021414 A1 | 1/2008 | Alheidt |
| 2008/0221531 A1 | 9/2008 | Alheidt et al. |
| 2008/0262439 A1 | 10/2008 | Alheidt |
| 2008/0300550 A1 | 12/2008 | Schiller et al. |
| 2008/0300551 A1 | 12/2008 | Schiller et al. |
| 2009/0048560 A1 | 2/2009 | Caizza et al. |
| 2009/0062736 A1 | 3/2009 | Jan |
| 2009/0076450 A1 | 3/2009 | Caizza et al. |
| 2009/0088724 A1 | 4/2009 | Chebator et al. |
| 2009/0093793 A1 | 4/2009 | Gross et al. |
| 2009/0171285 A1 | 7/2009 | Wang |
| 2009/0177156 A1 | 7/2009 | MacLean |
| 2009/0287161 A1 | 11/2009 | Traub et al. |
| 2009/0318880 A1 | 12/2009 | Janish |
| 2010/0076370 A1 | 3/2010 | Howlett et al. |
| 2010/0174236 A1 | 7/2010 | Burns et al. |
| 2010/0274190 A1 | 10/2010 | Wayman |
| 2010/0286609 A1 | 11/2010 | Mahurkar |
| 2010/0286610 A1 | 11/2010 | Chang |
| 2013/0218097 A1 | 8/2013 | Alheidt et al. |

FOREIGN PATENT DOCUMENTS

| | | |
|---|---|---|
| CN | 1874815 A | 12/2006 |
| DE | 202005004079 U1 | 7/2006 |
| EP | 0627231 A2 | 12/1994 |
| GB | 622848 A | 5/1949 |
| JP | 2004504895 A | 2/2004 |
| JP | 2006501944 A | 1/2006 |
| JP | 2008119075 A | 5/2008 |
| JP | 2008526363 A | 7/2008 |
| JP | 2009028527 A | 2/2009 |
| JP | 2009082715 A | 4/2009 |
| JP | 2009106687 A | 5/2009 |

OTHER PUBLICATIONS

Final Office Action in U.S. Appl. No. 13/871,682 dated Dec. 1, 2014, 10 pages.
Non-Final Office Action in U.S. Appl. No. 12/833,432 dated Mar. 30, 2012, 9 pgs.
Non-Final Office Action in U.S. Appl. No. 12/833,551, dated May 25, 2012, 13 pgs.
Non-Final Office Action in U.S. Appl. No. 13/871,682 dated May 9, 2014, 8 pages.
PCT IPRP & Written Opinion in PCT/US2010/041579, dated Jan. 10, 2012, 9 pgs.

__US 10,463,798 B2__

FLUSH SYRINGE WITH CONTROLLED PULSATILE FLUSHING

CROSS-REFERENCE TO RELATED APPLICATIONS

This application is a continuation of U.S. patent application Ser. No. 14/798,648, filed Jul. 14, 2015; which is a continuation of U.S. patent application Ser. No. 13/871,682, filed Apr. 26, 2013, now U.S. Pat. No. 9,084,851, issued Jul. 21, 2015; which is a continuation of U.S. patent application Ser. No. 12/833,551, filed Jul. 9, 2010, now U.S. Pat. No. 8,491,537, issued Jul. 23, 2013; which claims the benefit of priority from U.S. Provisional Application No. 61/224,688, filed Jul. 10, 2009, the disclosures of which are hereby incorporated in their entireties by reference thereto.

TECHNICAL FIELD

Aspects of the present invention relate to flush syringe assemblies that provide controlled pulsatile flushing of catheters and other vascular accessing devices (VADs) and methods of flushing a catheter.

BACKGROUND

VAD's are commonly used therapeutic devices and include IV catheters. There are two general classifications of VAD's, peripheral catheters and central venous catheters. If not properly maintained, VAD's can become occluded. To ensure VAD's are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Flush procedures require different types and amounts of flush solutions. The most commonly used flush solutions are saline and or heparin lock solution. The type of flush solution and amount vary depending on the specific type of catheter. Flush solution volumes between 5 and 10 ml are most common but can range from 1 ml to 20 ml.

For flush procedures, an I.V. line refers to a system containing a VAD, a tubing set with clamp and may terminate with a port or valve. The most common types of ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula in order to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip of a syringe barrel to allow fluid communication between the interior of the syringe and the catheter. These valves may contain structure for delivering fluid from a storage compartment in the valve to the catheter, and are referred to in the art as positive displacement valves. Such a valve is disclosed in U.S. Pat. No. 6,206,861.

Flush procedures may be enhanced by use of a "start-stop," "push-pause" (also referred to as "push-pulse") or turbulent flushing technique to remove debris or residue in the catheter that may cause occlusion or other undesirable effects. The removal of debris or residue is referred to as purging and prevents the build-up of deposits of blood, blood residue and IV drugs within a catheter or other VAD device. Such build-up can cause partial or complete blockage of the fluid pathway in a catheter system and can also require expensive and potentially dangerous methods for purging the affected catheter or a total catheter exchange. Often, such blockages lead to interruptions in therapy that may compromise patient care. The build-up of residue within a catheter can also increase infection risk by providing a breeding medium for microorganisms. For this reason, push-pulse is traditionally taught to healthcare workers.

As is understood by one skilled in the art, the push-pulse flushing technique introduces or creates turbulence within the syringe barrel when uneven pressure or force is applied to the plunger rod in the distal direction as the distal end of the plunger rod moves toward the barrel wall during expulsion of the flush solution contained within the barrel. In this disclosure, a convention is followed wherein the distal end of the device is the end closest to a patient and the proximal end of the device is the end away from the patient and closest to a practitioner. When such techniques are used in conjunction with catheters, turbulence is introduced within the catheter. Pulsing flow causes a swirling effect that moves any debris or residue attached to the catheter. Pulsing flow may also be referred to as pulsating flow and/or turbulent flow and includes flow that has a chaos or variations in its flow profile. Pulsing flow can be provided in a relatively controlled manner by a syringe that includes a plunger rod that interacts with the syringe barrel as the plunger rod is pushed forward to automatically create sharp pulses in fluid flow and pressure. In contrast to push-pulse and controlled pulsatile flow, conventional or "smooth" (also referred to as "straight" or "laminar") flushing techniques require the application of substantially constant pressure or force to the plunger rod in the distal direction. Conventional or smooth flushing techniques may also include the application of pressure or force that increases or decreases substantially linearly to the plunger rod in the distal direction.

However, the use of features that provide the force differential that creates pulsing fluid flow generally cannot be applied with infusion pumps or other delivery systems that require slow and controlled delivery of medication to patients. For example, certain infusion pumps have high pressure alarms and the forces and/or pressures created by push-pulse techniques of flushing can set off the high pressure alarm. In addition, push-pulse techniques and flush syringes that provide push-pulse techniques often do not provide a way to control the increases in pressure within the flush syringe. Typical flush syringes that incorporate physical barriers to create pulsatile movement of the plunger rod through the barrel rely on the user to apply increased force on the plunger rod so the plunger rod can overcome the physical barriers. Other flush syringes without such physical barriers also rely on the user to stop and start movement of the plunger rod within the barrel to create pulsatile movement of the plunger rod. In these and other known flush syringes and procedures for, the user may exert a force on the plunger rod that could cause the pressure within the barrel to increase up to 25 psi and above. These pressure levels within the barrel can lead to overpressurizing catheters or other VADs that can also lead to interruptions in therapy that may compromise patient care. Further, high pressures within the barrel during flushing can also lead to vein blowout.

There is a need for a flush syringe assembly that can be used with manual IV therapies and therapies that use infusion pumps and that provide controlled pulsatile flushing.

SUMMARY

A first aspect of the present invention pertains to a flush syringe assembly. In one or more embodiments, the flush syringe assembly includes a barrel with a first pulsing element, a plunger rod with a second pulsing element disposed within the barrel, a thumb press attached to one end of the plunger rod, a pulse control element disposed between the thumb press and the plunger rod. The flush syringe assembly also includes a stopper attached to the other end of the plunger rod to form a fluid-tight seal with the inside surface of the barrel. The chamber of the barrel may include a pre-selected amount of flush solution in the chamber. The flush solution may include saline and/or heparin.

The first pulsing element of the barrel and the second pulsing element of the plunger rod engage to provide an engagement force that causes pulsatile movement of the plunger rod as it moves within the barrel in the distal direction. The engagement force may be described as resisting a distally directed force applied to the plunger rod. In one or more embodiments, the second pulsing element may be aligned to prevent engagement with the first pulsing element to cause continuous and unimpeded movement of the plunger rod as it moves within the barrel in the distal direction. The first pulsing element may be provided as a retaining ring disposed on the barrel that extends inwardly into the chamber of the barrel. The second pulsing element may be provided as a plurality of projections disposed along the plunger rod body that extend outwardly from the plunger rod body. The plurality of projections may be disposed at regular intervals along the plunger rod body.

The barrel may include a side wall with an inside surface defining a chamber for retaining fluid. The barrel may include an open proximal end and a distal end including a distal wall with a tip extending distally therefrom having a passageway therethrough in fluid communication with the chamber. The plunger rod disposed within the barrel includes a distal end, a proximal end, and a plunger rod body extending from the distal end to the proximal end. The second pulsing element may be disposed on the plunger rod body. The thumb press is slidably attached to the proximal end of the plunger rod.

The pulse control element of one or more embodiments may include a spring or a compression spring that compresses to provide a compression force upon application of a distally directed force on the thumb press and expands as the distally directed force is released. In one or more embodiments, the spring has a spring rate so that application of a continuous distally directed force on the thumb press increases the compression force until it is greater than the engagement force and causes the first pulsing element to disengage from the second pulsing element permitting the plunger rod to move in a distal direction. In another variant, the spring rate is such that the disengagement of the first pulsing element and the second pulsing element causes the spring to expand and the compression force to decrease.

In one or more embodiments, the thumb press includes a proximal end, a distal end, and a plurality of engagement tabs disposed at the distal end of the thumb press. The plunger rod of one or more embodiments may include a plurality of openings having a distal end, a proximal end and a length between the distal end and the proximal for receiving the engaging tabs. When the engagement tabs are engaged with the openings of the plunge rod, the engagement tabs may be configured to slide along the length of the plurality of openings as the compression force is applied to the thumb press in the distal direction and the compression force is released. Stated in other words, when the engagement tabs are engaged with the openings of the plunge rod, the engagement tabs may be configured to slide along the length of the plurality of openings as the a force is applied to the thumb press in the distal direction to cause the spring to compress and the same force is released. Therefore, in one or more embodiments, the expansion of the spring may also cause the engagement tabs to slide to the distal end of the plurality of openings and the compression of the spring allows the engagement tabs to slide to the proximal end of the plurality of openings.

In one or more embodiments, the thumb press may also include a locking element that engages with the first pulsing element to lock the thumb press at least partially within the barrel when the stopper is in contact with the distal wall of the barrel. When at least a portion of the thumb press is locked within the barrel, the pulse control element exerts a force on the plunger rod in a distal direction.

In one or more embodiments, the flush syringe assembly may include a barrel, a plunger rod disposed within the barrel and a stopper disposed on a distal end of the plunger rod for forming a fluid-tight seal with the inside surface of the barrel. In one or more embodiments, the barrel includes a side wall having an inside surface defining a chamber for retaining fluid. The barrel may also include an open proximal end and a distal end including a distal wall with a tip extending distally therefrom having a passageway therethrough in fluid communication with said chamber. The open proximal end of the barrel includes at least one protrusion extending inwardly into the chamber. The barrel may also include a pre-selected amount of flush solution in the chamber. The flush solution may include saline or heparin.

The plunger rod includes a distal end, a proximal end including a thumb press, a compressible plunger rod body extending from the distal end to the proximal end. The plunger rod body includes a plurality of projections disposed along the plunger rod body that, upon application of a distally directed force to the thumb press, engage the protrusion of the barrel to provide an interference force with variations and cause pulsatile movement of the plunger rod as it moves within the barrel in the distal direction and imparts pulsing flow to the flush solution and increases the pressure of the flush solution. In one variant, the plurality of projections of the plunger rod may be aligned to prevent cooperation with the protrusion of the barrel to cause continuous and unimpeded movement of the plunger rod as it moves within the barrel in the distal direction. The proximal end of the barrel comprises a portion that is free of any protrusions. In one or more embodiments, the plunger rod may be rotatable within the barrel such that the plurality of projections may be aligned with the portion that is free of any protrusions to cause continuous and unimpeded movement of the plunger rod as it moves within the barrel in the distal direction.

The plunger rod body may include a hollow portion including a spring having a rate so that the spring is initially compressed to provide a force that is less than the interference force and upon further application of distally direct force to the thumb press, the spring is compressed to provide sufficient force that is greater than the interference force.

In one or more embodiments, the compressible plunger rod body includes a telescoping segment attached to the proximal end of the plunger rod. The telescoping segment may be configured to slide in and out of the plunger rod body to reduce and increase the length of the plunger rod body. In such embodiments, the spring may be disposed between the telescoping segment and the plunger rod body. The spring may compress to generate a compression force as a force is applied to the plunger rod in the distal direction and expand as the compression force is released. In one or more embodiments, the expansion of the spring causes the telescoping segment to slide out of the plunger rod body to increase the length of the plunger rod body and the compression of the spring allows the telescoping segment to slide into the plunger rod body to reduce the length of the plunger rod body.

In one or more embodiments, the interaction of the plurality of projections with the protrusion of the barrel generates an engagement force that exerts a force on the plunger rod in a proximal direction. In such embodiments, increasing the compression force allows the plunger rod to overcome the engagement force and causes the plurality of projections to disengage from the protrusion. The disengagement of the plurality of projections and the protrusion causes the compression force to decrease.

The plunger rod of one or more embodiments may include a locking element that engages with the protrusion of the barrel to lock at least a portion of the plunger rod within the barrel when the stopper is in contact with the distal wall of the barrel. The locking of at least a portion of the plunger rod within the barrel causes the spring to exert a force on the plunger rod in a distal direction.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

A first aspect of the present invention pertains to a flush syringe assembly configured to permit pulsatile movement of the plunger rod. The pulsatile movement of the plunger rod imparts pulsing flow to the flush solution as it is expelled. The first aspect of the present invention also includes flush syringe assemblies with a pulse control element to control the pressure of the flush solution being expelled by the flush syringe assembly. A flush syringe assembly 100 according to an embodiment of the first aspect of the present invention is shown in FIGS. 1-16.

Figure 1:
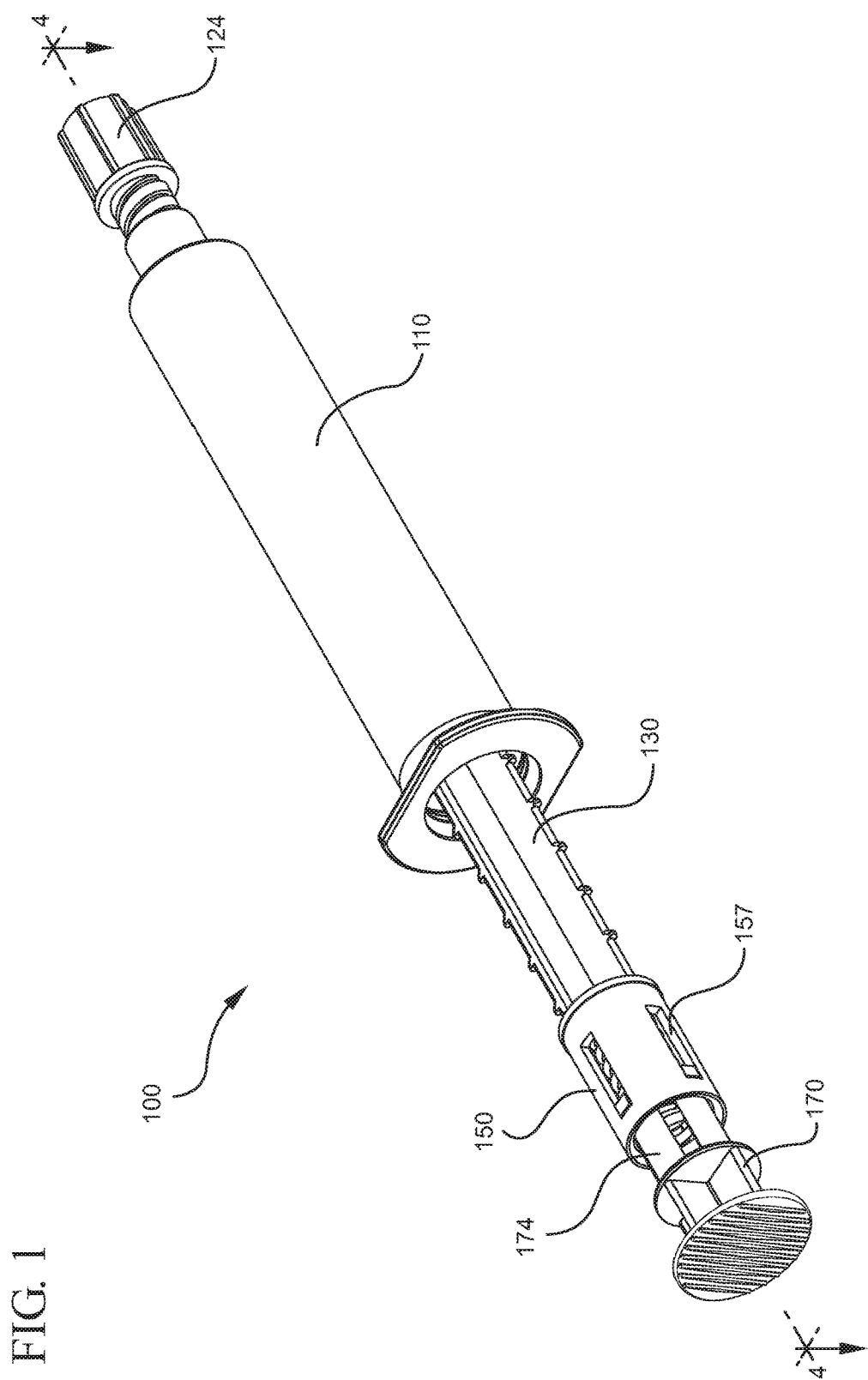
FIG. 1 show a perspective view of an embodiment of a flush syringe assembly including a thumb press, a pulse control element, a plunger rod, a stopper, a syringe barrel and tip cap.
Figure 2:
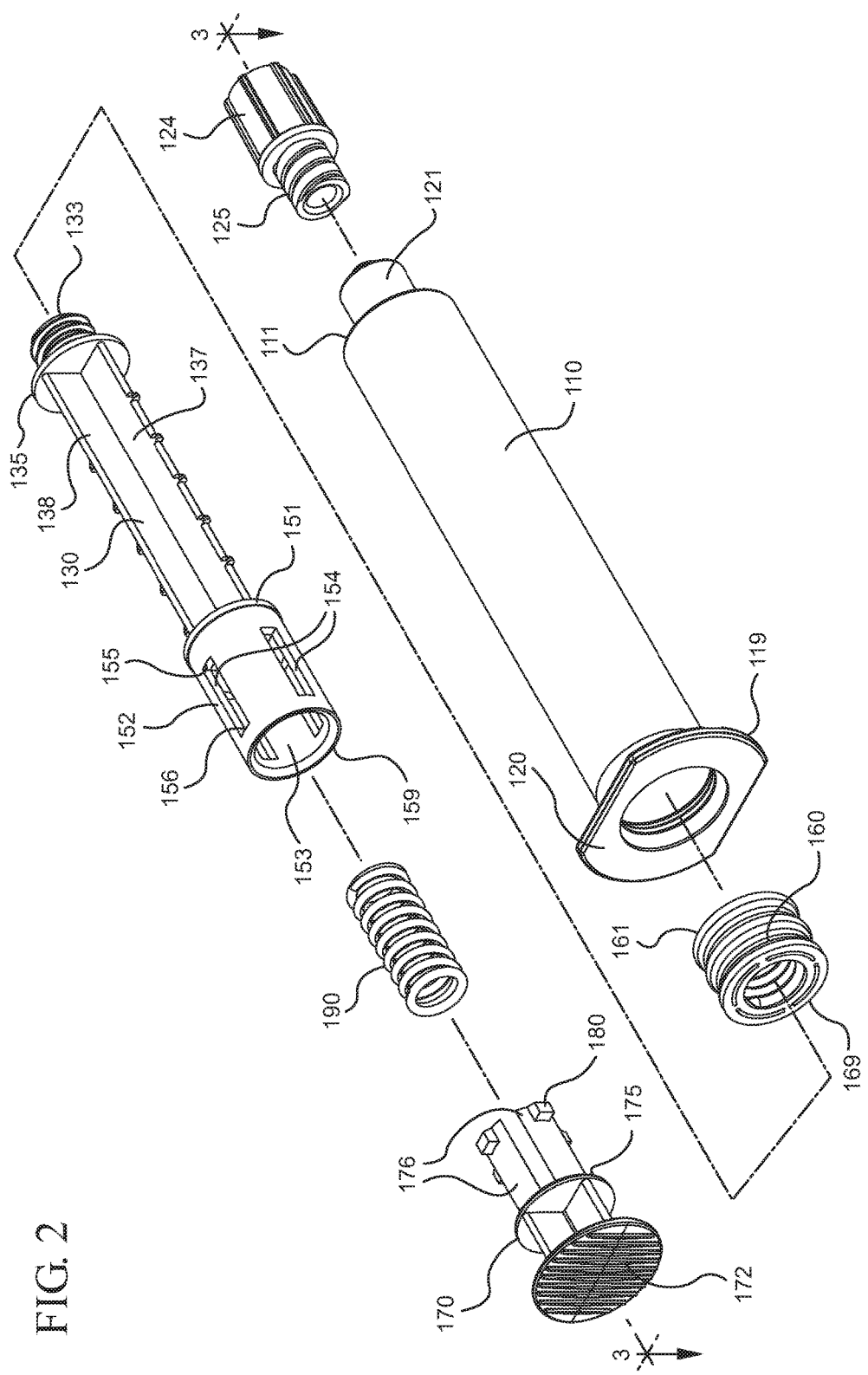
FIG. 2 shows an exploded perspective view of the flush syringe assembly of FIG. 1.
Figure 3:
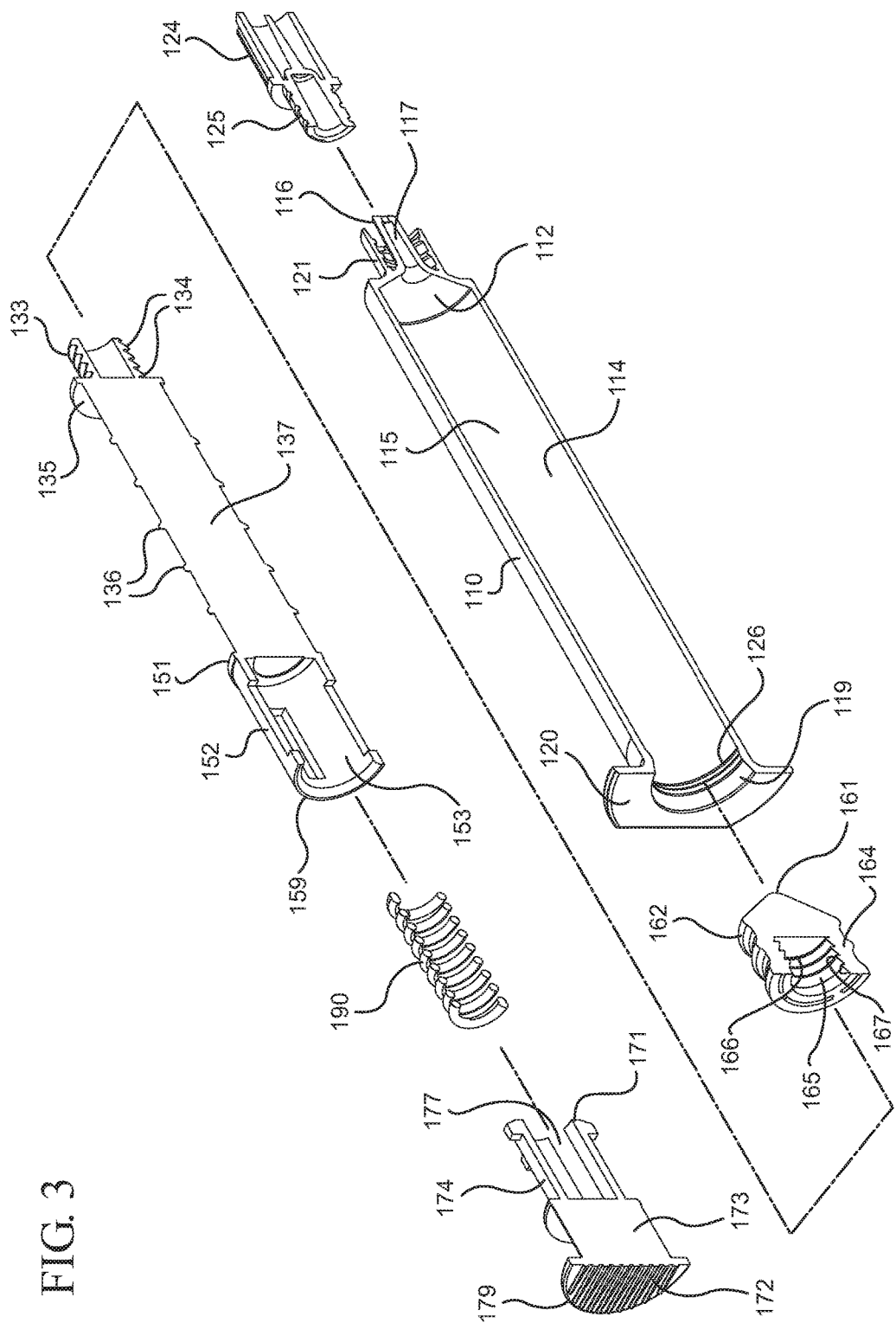
FIG. 3 illustrates a cross-sectional view taken along line 3-3 of the flush syringe assembly shown in FIG. 2.
Figure 4:
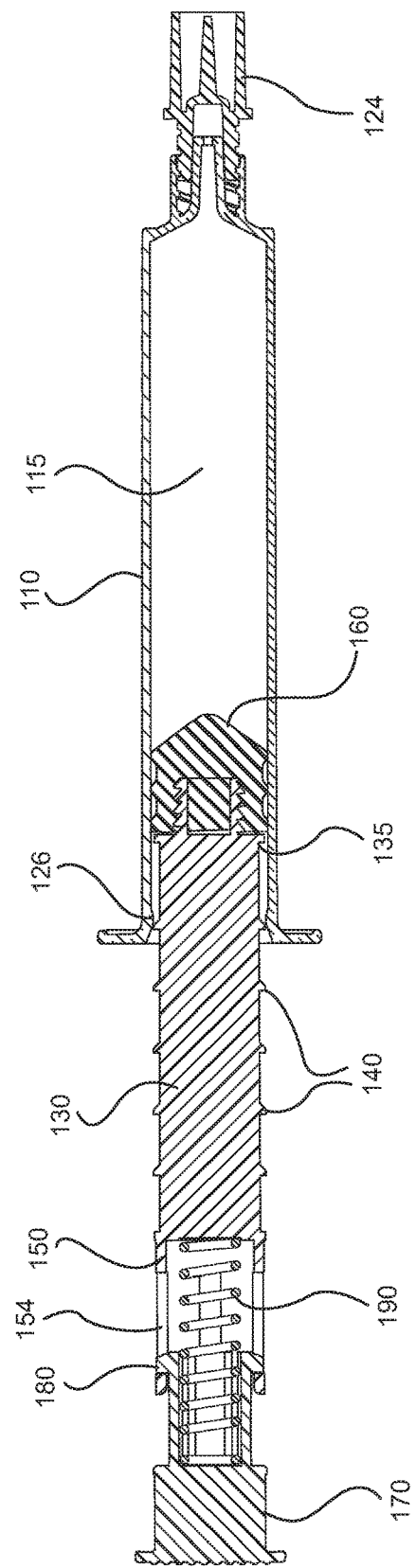
FIG. 4 illustrates a cross-sectional side view taken along line 4-4 of the flush syringe assembly shown in FIG. 1.
Figure 5:
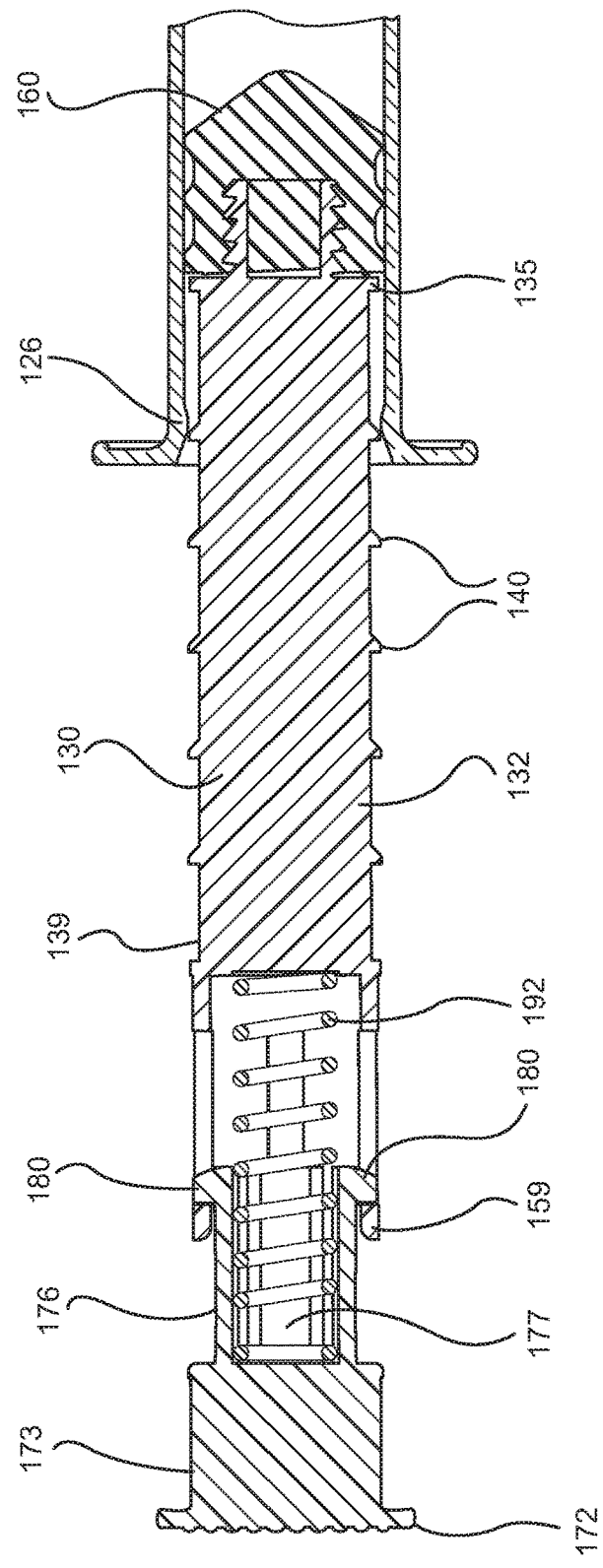
FIG. 5 illustrates an enlarged partial view of the flush syringe assembly shown in FIG. 4.

FIG. 1 shows the flush syringe assembly 100 in an assembled state. The flush syringe assembly 100 includes a syringe barrel 110, a plunger rod 130 disposed within the syringe barrel 110, a stopper 160 attached to one end of the plunger rod 130, a thumb press 170 attached to the second end of the plunger rod 130 and a pulse control element 190 disposed between the thumb press 170 and the plunger rod 130.

The syringe barrel 110 includes 110 includes an open proximal end 119 and a distal end 111 and a distal wall 112. A sidewall 113 extends from the distal end 111 to the open proximal end 119 and includes an interior surface 114 that defines a chamber 115 for retaining or holding fluids, which may include flush solution and/or other liquids. The distal end 111 may also include a tip 116 having an open passageway 117 therethrough in fluid communication with the chamber 115. The syringe barrel 110 may include an optional finger flange 120 at the open proximal end 119 extending radially outwardly from the sidewall 113. The distal end 111 of the syringe barrel 110 includes a threaded collar 121 surrounding the tip 116 that forms a channel 122 for receiving a tip cap 124. The tip cap 124 more clearly shown in FIG. 2 includes a threaded portion 125 that is inserted into the channel 122 and engages the threaded collar 121 of the syringe barrel 110. The threaded collar 121 may also engage a needle hub (not shown).

The syringe barrel 110 includes a first pulsing element 126 that is configured to cooperate with the plunger rod or engage a portion of the plunge rod to cause pulsatile movement of the plunger rod as it moves within the barrel in at least the distal direction. The first pulsing element 126 is configured to cooperate or engage a portion of the plunger rod to cause pulsatile movement of the plunger rod as it moves within the barrel in the distal direction and proximal directions. In the embodiment shown, the first pulsing element 126 is disposed on the interior surface 114 of the syringe barrel. Specifically, the first pulsing element 126 is shown as a structure that reduces the cross-sectional width of the interior surface 114 of the syringe barrel at or adjacent to the open proximal end 119 of the syringe barrel. It will be understood that the first pulsing element 126 may be disposed at other locations along the interior surface 114 of the syringe barrel. In one variant, the first pulsing element 126 may be a separate component (not shown) attached to the open proximal end 119 of the syringe barrel that reduces the cross-sectional width of the open proximal end 119 of the syringe barrel. In another variant, the first pulsing element 126 may include a plurality of inwardly extending projections (not shown) disposed along the length of the interior surface 114 of the syringe barrel. The first pulsing element 126 may be provided in the form of a plurality of inwardly projecting rings (not shown) that extends around the circumference of the interior surface 114 and are disposed at intervals along the length of the barrel.

In the embodiment shown in FIGS. 1-16, the first pulsing element 126 is formed by a retaining ring 127 (shown in FIG. 8) that extends into the chamber 115. The retaining ring may be described as an inwardly extending protrusion. The cross-sectional width of the interior surface 114 of the syringe barrel at the retaining ring 127 is less than the cross-sectional width of the interior surface 114 at the remaining portions of the syringe barrel. The interior surface 114 of the syringe barrel 110 may include an inclined portion 128 disposed proximally adjacent to the retaining ring 127. The cross-sectional width of the interior surface 114 of the syringe barrel increases from the open proximal end 119 to the retaining ring 127. The interior surface 114 may also have a declined portion 129 disposed distally adjacent to the retaining ring 127. The interior surface 114 of the syringe barrel decreases from the retaining ring 127 to the distal end 111 of the syringe barrel.

The retaining ring 127 may be provided as a separate component. The separate retaining ring (not shown) may be provided in the form of a disc with an opening in the center of the disc. The disc and/or opening would be sized and shaped so the retaining ring 127 may be to be fitted onto the open proximal end 119 of the barrel. The separate retaining ring would include at least one extension that extends from the disc into the opening. The cross-sectional width of the opening is decreased at the extension. The remaining portions of the opening are free of extensions. The cross-sectional width of the opening at these remaining portions is greater than the cross-sectional width of the opening at the extension. The separate retaining ring may be rotated with respect to the syringe barrel or the syringe barrel and the separate retaining ring may be rotated such that the position of the extension can change with respect to the plunger rod. The extension may be aligned with the plunger rod such that the extension engages with the plunger rod to create pulsatile movement of the plunge rod. Alternatively, the plunger rod may be aligned with the portions of the opening that are free of extensions so there is no engagement between the extension and the plunger rod and the plunger rod may move within the barrel in a continuous and unimpeded manner. Such embodiments would enable the user to utilize existing syringe barrels with the plunger rods described herein in flushing procedures.

Still referring to FIGS. 1-16, the side wall 113 of the syringe barrel may be cylindrical or may have another shape. In addition, the chamber 115 of the syringe barrel may include a desired amount of flush solution. The sidewall 113 may also include measuring indicia to indicate the amount of flush solution contained within the chamber 115.

The flush syringe assembly may be pre-filled with flush solution during or after the assembly of the syringe using sterile filling methods. In such prefilled syringes, the tip cap 124 is attached to the tip 116 to seal the passageway 117 of the barrel. In embodiments in which the chamber 115 is provided empty, to fill the chamber 115 with the desired amount of flush solution, a needle assembly or hub may be attached to the tip 116. The needle assembly would include a needle cannula to pierce a pierceable septum or to be inserted into a pre-split septum of a vial or neck of a glass ampoule containing flush solution and the flush solution is drawn into the chamber 115 of the syringe barrel by pulling plunger rod 130 in the proximal direction while holding barrel, to draw fluid through the needle cannula into chamber 115.

Exemplary flush solutions include saline flush solution and/or heparin lock flush solution. These solutions are known in the art and readily available. An example of a saline flush solution is 0.9% Sodium Chloride USP for injection. An example of a heparin lock flush solution is 0.9% Sodium Chloride with 100 USP units of Heparin Sodium per ml or 10 USP units of Heparin Sodium per ml.

As shown in FIGS. 1-5, the plunger rod 130 is disposed within the chamber 115 of the syringe barrel. The plunger rod 130 includes a distal end 131 and a proximal end 139. A stopper 160 is attached to the distal end 131 of the plunger rod 130 and includes a sealing edge 162 for forming a fluid tight seal with the interior surface 114 of the syringe barrel to draw fluid into the chamber 115 and to drive fluid out of the chamber 115. The stopper 160 includes a distal end 161, a proximal end 169 and a stopper body 164 that extends from the distal end 161 to the proximal end 169. The stopper body 164 includes an interior recess 165 defined by an inside surface 166 for receiving at least a portion of the plunger rod 130.

The stopper 160 shown in FIGS. 1-16 includes a distal end 161 having a conical shape. Accordingly, when the distal end 161 of the stopper is in contact with the distal wall 112 of the syringe barrel, the stopper 160 is in full contact with the distal wall 112 and drives as much of the flush solution out of the chamber 115 as possible.

In the embodiment shown, the distal end 131 of the plunger rod includes a distal attachment portion 133 that includes a plurality of plunger rod threads 134 disposed thereon for engaging corresponding stopper threads 167 disposed on the inside surface 166 of the stopper 160. To attach the stopper 160 to the plunger rod 130, the distal attachment portion 133 is inserted into interior recess 165 of the stopper 160 and one or both of the plunger rods 130 and the stopper 160 is rotated with respect to one another until the plurality of plunger rod threads 134 engages the stopper threads 167. In one or more embodiments, the distal attachment portion 133 and the inside surface 166 of the stopper 160 may include corresponding structure to enable a friction interference fit, snap fit or other connection to attach the stopper 160 to the plunger rod 130. In one variant, the distal end 131 of the plunger rod 130 may include an integrally formed sealing portion (not shown) that forms a fluid-tight seal with the interior surface 114 of the syringe barrel.

The plunger rod 130 includes an optional annular protrusion 135 that extends radially outwardly from the plunger rod body and is disposed proximally adjacent to the distal attachment portion 133. The annular protrusion 135 provides stability to the plunger rod during use and/or provides a physical barrier to engagement between the plunger rod threads 134 and the stopper threads 167.

The plunger rod 130 includes a plunger rod body 132 that extends from the annular protrusion 135 to the proximal end 139 of the plunger rod. In embodiments that do not utilize an annular protrusion 135, the plunger rod body 132 extends from the distal end 131 to the proximal end 139 of the plunger rod. In the embodiments shown in FIGS. 1-16, the plunger rod body 132 includes an outside surface that forms a perimeter around the plunger rod body 132 and an axial length extending along the length of the plunger rod body 132. The plunger rod body 132 may include a single beam or structure, which may have cylindrical or other shapes. As shown in FIGS. 1-16, the plunger rod body 132 may be formed by two perpendicularly intersecting beams 137, 138. The beams may each have a rectangular cross-section. In the embodiment shown, the two intersecting beams 137, 138 intersect to form an outside surface defining four quadrants 144, 145, 146, 147 (shown more clearly in FIG. 7A) that are open and face the interior surface 114 of the syringe barrel and extend along the axial length from the proximal end 139 to the annular protrusion 135 of the plunger rod.

In the embodiments shown in FIGS. 1-16, the plunger rod 130 includes a second pulsing element 136 that is disposed on the outside surface of the plunger rod body 132. The second pulsing element may be integrally formed or may be provided as separate components that may be attached to the outside surface of the plunger rod body 132. In such embodiments, the plunger rod may further include structure for the attachment of a separate second pulsing element 136 to the outside surface of the plunger rod body 132.

Figure 7:
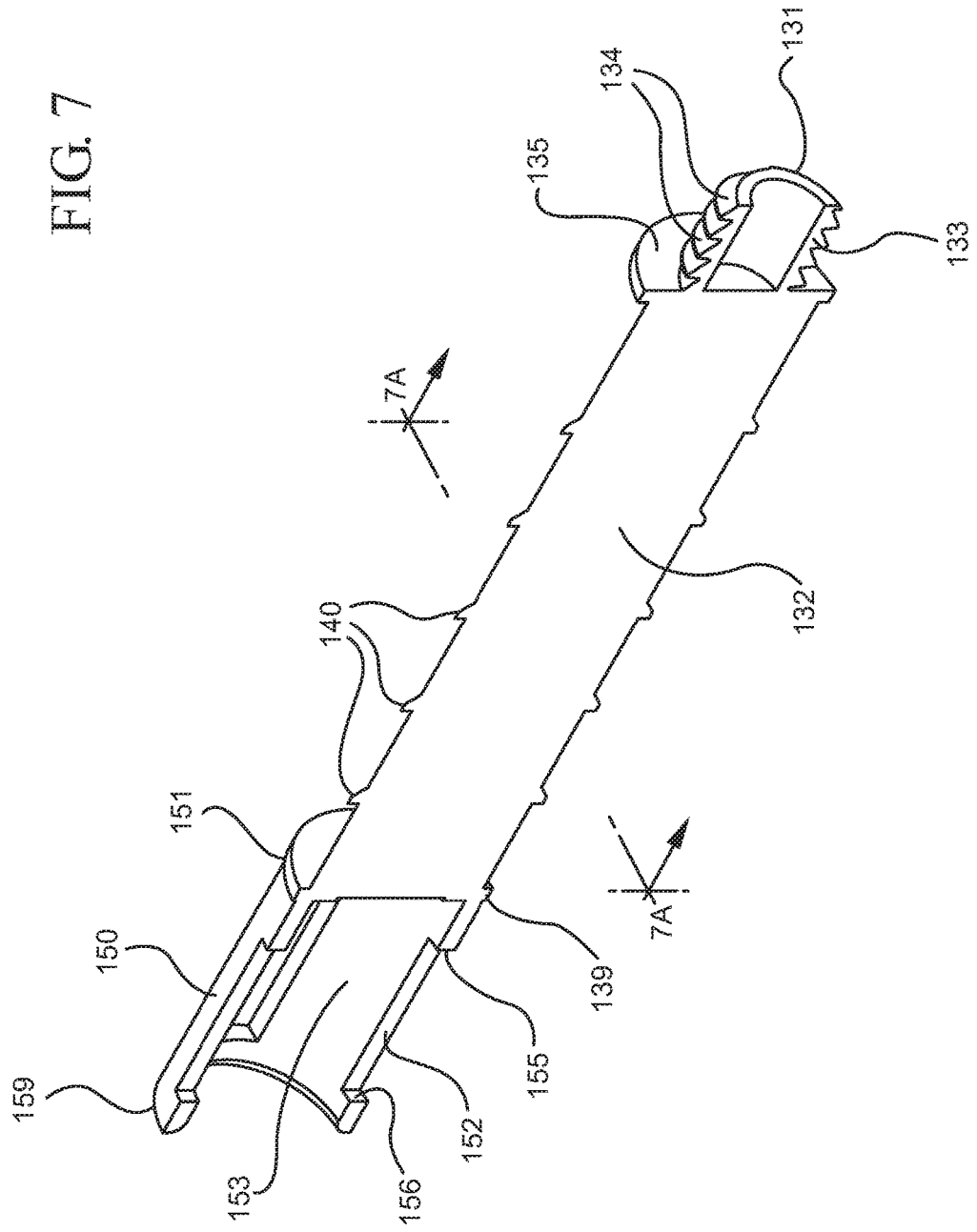
FIG. 7 illustrates the plunger rod as shown in FIG. 3.
Figure 7B:
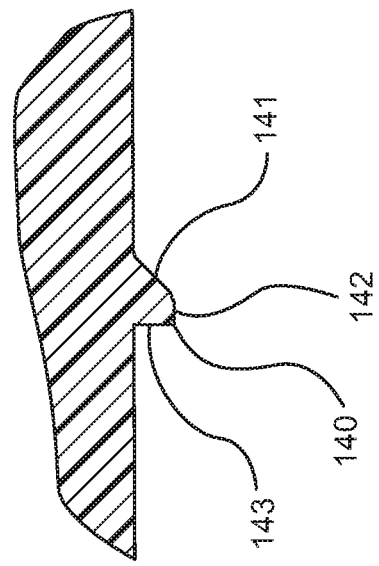
FIG. 7B is a enlarged partial side view of the plunger rod shown in FIG. 7.
Figure 7A:
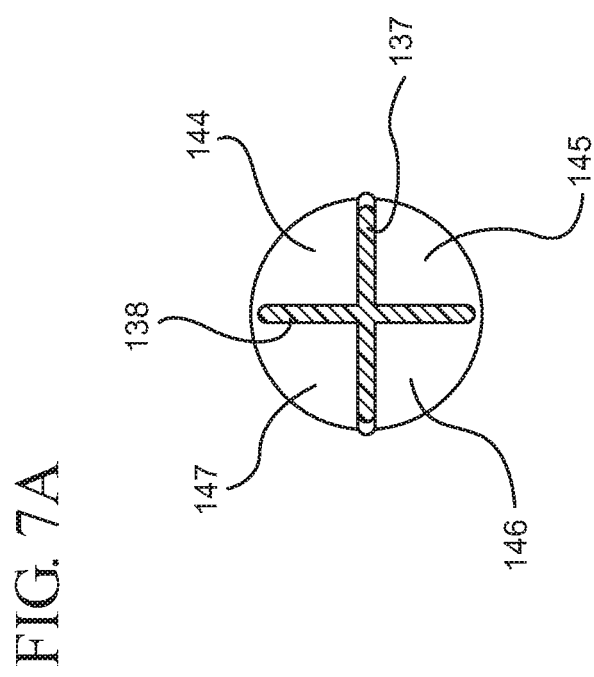
FIG. 7A is a cross-sectional view taken along line 7A-7A of the plunger rod shown in FIG. 7.
Figure 8:
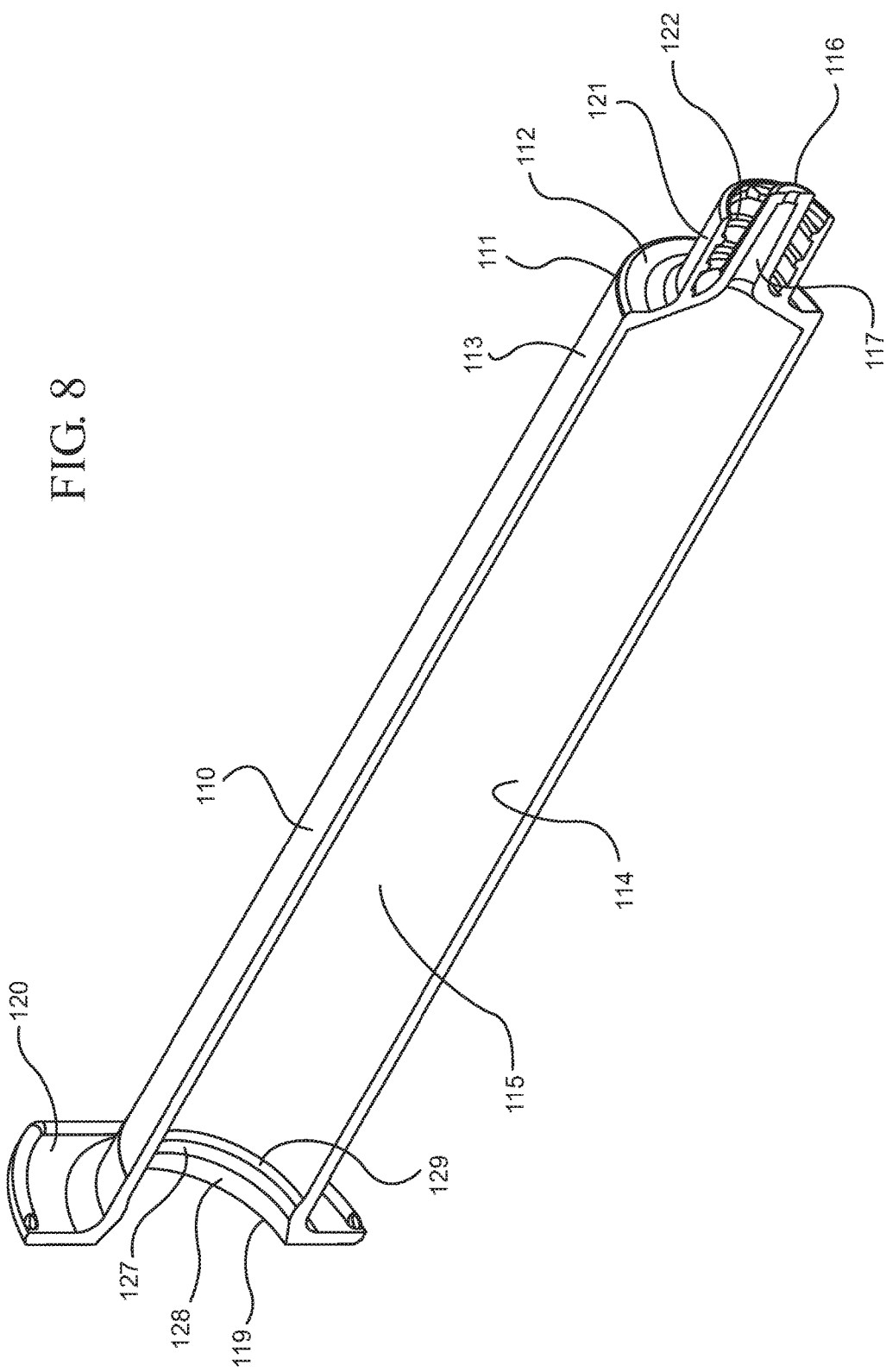
FIG. 8 illustrates the syringe barrel shown in FIG. 3.
Figure 8A:
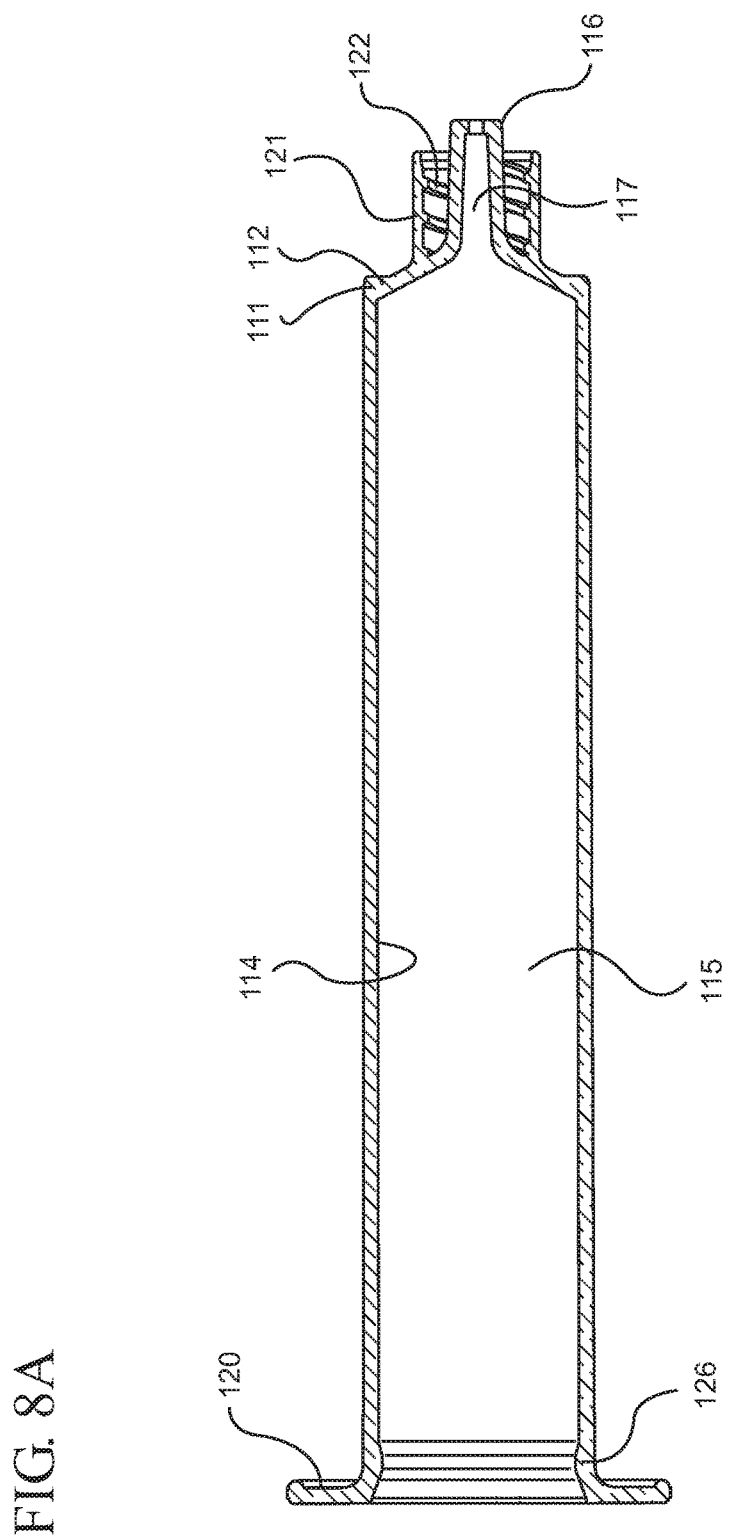
FIG. 8A illustrates a side view of the syringe barrel shown in FIG. 8.

In accordance with the embodiments shown more clearly in FIGS. 7 and 7A, the second pulsing element 136 is provided as a plurality of projections 140 disposed along the length of the plunger rod body 132 at regular intervals. In one or more embodiments, the second pulsing element 136 may be provided as a single projection (not shown) that engages with the first pulsing element 126 of the syringe barrel that includes a plurality of retaining rings 127 (not shown) disposed along the length of the interior surface 114 of the syringe barrel.

In embodiments utilizing two perpendicularly intersecting beams 137, 138 to form the plunger rod body 132, the second pulsing element 136 may be disposed at opposite ends of one beam, as shown in FIG. 7A. In another variant, the second pulsing element 136 may be disposed on opposite ends of both beams 137, 138. In embodiments utilizing a single beam or structure to form a plunger rod body, second pulsing element 136 may be disposed around the perimeter of the plunger rod body 132 at regular intervals. Optionally, the second pulsing element may be formed along a segment of the perimeter of the plunger rod, while the remaining segments of the outside surface are free of the second pulsing element. In such embodiments, the second pulsing element 136 may extend along the entire axial length. In a specific embodiment, the second pulsing element may be formed along two opposite segments of the perimeter of the plunger rod body, leaving two opposite segments of the perimeter of the plunger rod that are free of protrusions. In such embodiments, the second pulsing element 136 may also extend along the entire axial length.

In embodiments where the second pulsing element 136 is disposed on opposite ends of one beam, where two beams are used to form the plunger rod body 132 or the second pulsing element 136 is disposed at one or more segments of the perimeter of the plunger rod body 132 or other embodiments in which the second pulsing element 136 is positioned so it is not always in contact with the first pulsing element 126 while the plunger rod 130 is disposed within the syringe barrel 110, the position of the second pulsing element 136 permits the plunger rod 130 to move in a pulsatile or continuous and unimpeded manner within the syringe barrel 110. Moreover, such positions of the second pulsing element 136 also permit the user to select whether to impart pulsing flow to the flush solution being expelled by selecting whether the plunger rod 130 should move in a pulsatile manner or continuous and unimpeded manner within the syringe barrel 110. The user would select between moving the plunger rod 130 in a pulsatile manner or continuous and unimpeded manner by rotating the plunger rod 130 so that the second pulsing element 136 does not engage or interact with the first pulsing element 126.

In one or more embodiments, the plunger rod 130 may include a second pulsing element 136 that is shaped, positioned or otherwise disposed on the plunger rod boy 132 in such a manner that forces the user to impart pulsing flow to the flush solution being expelled because it forces alignment of the second pulsing element 136 with the first pulsing element 126 such that they must engage or interact. The first pulsing element 126 may also be shaped, positioned or disposed on the syringe barrel 110 such that engagement or interaction with the second pulsing element 136 cannot be avoided during use and the plunger rod 130 is only able to move in a pulsatile manner within the syringe barrel.

In the embodiment shown in FIGS. 7 and 7A, the plurality of projections 140 include a distally facing ramped surface 141 disposed that extends from the plunger rod body 132 such that the cross-sectional width of the plunger rod body 132 increases along the ramped surface 141 in the proximal direction. The plurality of projections 140 may also include a projection surface 142 disposed proximally adjacent to the ramped surface 141 and a perpendicular surface 143 disposed proximally adjacent to the projection surface 142. The cross-sectional width of the plunger rod body 132 along the projection surface 142 may be constant or may optionally increase or decrease. In one or more alternative embodiments, the plurality of projections 140 may be provided as rounded extensions (not shown), where the cross-sectional width of the plunger rod body 132 increases proximally to a point and then decreases.

In one or more embodiments, the second pulsing element 136 may be provided in the form of partial discs (not shown) that extend between the two intersecting beams 137, 138. Specifically, the partial discs may be connected to the adjacent beams 137, 138 and extend radially outwardly toward the inside surface of the barrel from at least one of the quadrants 144, 145, 146, 147 formed by the beams 137,

138. In such embodiments, the cross-sectional width of the plunger rod body 132 increases at the quadrants in which the partial discs are disposed. Alternatively, the partial discs may be formed in two non-adjacent quadrants 144, 146 and connect between the beams 137, 138. The partial discs may be positioned at regular intervals along the axial length of the plunger rod body 132. In one or more alternative embodiments, the partial discs may be positioned at irregular intervals and/or may be positioned at or adjacent to the proximal end 139 or the annular protrusion 135 of the plunger rod.

The plurality of protrusions 140 may be provided as rings (not shown) that extend around the perimeter of the plunger rod body 132. The rings may be disposed at intervals along the axial length of the plunger rod body 132. The cross-sectional width of the plunger rod body 132 at the rings is greater than the cross-sectional width of the plunger rod body 132 at locations between the rings.

The plunger rod 130 also includes a proximal attachment portion 150 for attaching the thumb press 170 to the plunger rod in a frictional interference fit. The proximal attachment portion 150 may be attached or integrally formed at the proximal end 139 of the plunger rod. The proximal attachment portion 150 includes a closed distal end 151 adjacent to the proximal end 139 of the plunger rod, an open proximal end 159 and a proximal wall 152 extending from the distal end 151 to the proximal end 159. The proximal wall 152 includes an inside surface that defines a hollow interior 153 in fluid communication with the open proximal end 159 and the thumb press, as will be described herein. The hollow interior 153 is shaped to receive the pulse control element 190 and at least a portion of the thumb press 170. The open proximal end 159 may include an extending rim portion (not shown) that extends inwardly into the hollow interior 153 for retaining at least a portion of the thumb press 170 within the hollow interior 153 of the proximal attachment portion. The thumb press 170 may include a corresponding structure for engaging the rim portion.

The proximal wall 152 includes at least one opening 154 for engaging at least a portion of the thumb press 170. In the embodiment shown in FIGS. 2, 7 and 7A, the proximal wall 152 includes four openings 154 disposed at regular intervals along the proximal wall 152. Each of the four openings 154 has an elongate shape having a distal end 155, a proximal end 156 and a length 157 that extends therebetween. The length 157 of the opening 154 permits a portion of the thumb press 170 to slide from the distal end 155 of the opening 154 to the proximal end 156 of the opening. As will be described in more detail below, the length 157 of the opening 154 allows the thumb press to move relatively to the plunger rod. The length 157 also permits the combined length of the plunger rod 130 and the thumb press 170 to expand or increase and compress or decrease. Such relative movement or expansion and compression permits the pulse control element disposed between the thumb press 170 and the plunger rod 130 to expand and compress.

The proximal wall 152 is shown as having a circular cross-section, however, it will be understood that the proximal wall 152 may shaped to have a square cross-section or other shaped cross-section. The openings 154 are also shown as having a generally rectangular configuration, however, it will be understood that the distal end 155 and/or proximal end 156 of the opening 154 may be rounded or shaped otherwise.

In the embodiment shown, the thumb press 170 is attached to the proximal attachment portion 150 in a frictional interference fit. The thumb press 170 may alternatively include a threaded portion (not shown) that engages with a corresponding structure on the open proximal end 159 of the proximal attachment portion 150. The thumb press 170 includes an open distal end 171 in fluid communication with the open proximal end 159 of the proximal attachment portion 150 and a closed proximal end 179. A first annular disc 172 is attached to the proximal end 179 and provides a surface for the user to apply proximally directed and distally directed forces on the thumb press 170 and the plunger rod 130. The thumb press 170 includes a body portion 173 that extends from the first annular disc 172 to a plunger-engaging portion 174. A second annular disc 175 may optionally be disposed between the body portion 173 and the plunger-engaging portion. The second annular disc 175 may be shaped to lock the thumb press 170 into the syringe barrel with the first pulsing element 126. In other words, the thumb press 170 has a cross-sectional width at the second annular disc 175 that is greater than the cross-sectional width of the syringe barrel at the first pulsing element 126 such that once the second annular disc 175 advances distally past the first pulsing element 126, for example, the retaining ring 127, at least a portion of the thumb press 170 is locked within the syringe barrel 110. The second annular disc 175 may include a tapered surface (not shown) to facilitate movement distally past the first pulsing element 126 and may include a stop surface (not shown) to prevent movement of the thumb press in the proximal direction after the second annular disc 175 has moved distally past the first pulsing element 126. Alternatively, the body portion 173 may be shaped and/or may have a size to enable the user to lock the thumb press 170 into the syringe barrel with the first pulsing element 126.

The plunger-engaging portion 174 may be described as a telescoping segment of the plunger rod 130. In other words, the plunger-engaging portion 174 may be described as an extension of the plunger rod that is moveable relative to the plunger rod body in a telescoping fashion that causes the length of the plunger rod to expand and compress. The plunger-engaging portion 174 may also be described as a separate portion that allows the thumb press 170 to be slidable attached to the plunger rod.

In the embodiment shown, the plunger-engaging portion 174 includes a plurality of fingers 176 that extend distally from the second annular disc 175 and/or the body portion 173 of the thumb press 170 to the open distal end 171 of the thumb press. The plurality of fingers 176 defines a recessed portion 177 within the plunger-engaging portion 174. In the embodiment shown in FIG. 6, the recessed portion 177 has a circular cross-sectional shape; however, it may have any shape to accommodate the pulse control element 190.

Figure 6:
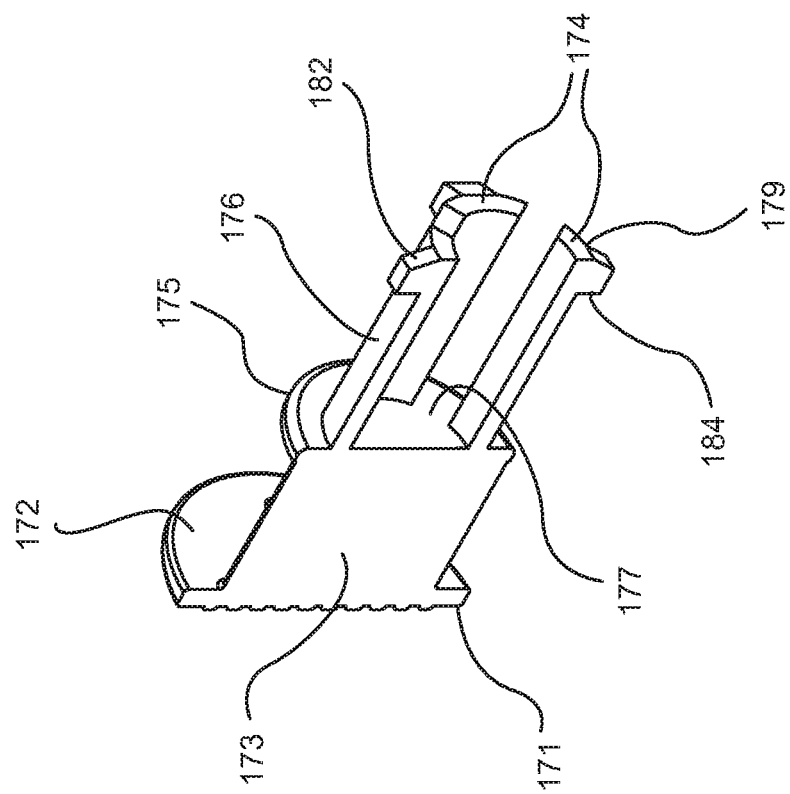
FIG. 6 illustrates the thumb press shown in FIG. 3.

In the embodiment shown in FIG. 6, the thumb press 170 includes four fingers 176. The four fingers 176 may also be described as a solid wall that extends distally from the second annular disc 175 and defines the recess portion 177 and includes four openings spaced around the solid wall. Outwardly projecting engagement tabs 180 are disposed on each of the plurality of fingers 176 for engaging the openings 154 of the proximal attachment portion 150. In the embodiment shown, the engagement tabs 180 are disposed adjacent to the open distal end 171 of the thumb press 170. The engagement tabs 180 may be shaped to have a tapered surface 182 adjacent to the distal end 171 of the thumb press and a locking surface 184 on the opposite end of the engagement tabs 180 from the tapered surface 182. The locking surface 184 is perpendicularly disposed with respect to the fingers 176 such that when engaged in the opening 154 of the proximal attachment portion 150, the locking surface 184 prevents the tab from disengaging from the opening 154. The shape of the fingers 176 and the tapered surface 182 of the engagement tabs 180, facilitate the initial engagement of the engagement tabs 180 with the openings 154 and attachment of the thumb press 170 to the plunger rod 130. Specifically, to assemble the thumb press 170 and the plunger rod 130, the fingers 176 are inserted into the hollow interior 153 of the proximal attachment portion. The engagement tabs 180 are aligned with the openings 154 such that the tapered surface 182 enters the openings 154 and the locking surface 184 engages with the openings. The fingers 176 may flex inwardly until the engagement tabs 180 enter the openings 154.

The length of the openings 154 permit relative motion between the thumb press 170 and the plunger rod 130. Specifically, when the engagement tabs 180 are disposed at the proximal end 156 of the openings 154, the length of the plunger rod 130 and the thumb press 170 is maximized. When a force is applied to the thumb press 170 in the distal direction, the thumb press 170 moves within the hollow interior 153 of the proximal attachment portion until the engagement tabs 180 slide toward the distal end 155 of the openings 154. In this position, the length of the plunger rod 130 and the thumb press 170 is reduced to its shortest length. The change in the relative position of the engagement tabs 180 with respect to the openings 154 indicates the amount of compression of the pulse control element 190, as will be described below.

A pulse control element 190 is disposed within the recessed portion 177 of the plunger-engaging portion 174 and extends into the hollow interior 153 of the proximal attachment portion 150. The pulse control element 190 is shown in FIGS. 1-16 as a spring that is compressible and can expand as the thumb press 170 moves in the proximal and distal directions, relatively to the plunger rod 130. The pulse control element 190 may be provided in the form of a spring 192. The spring 192 may be characterized as a compression spring. In one or more embodiments, the spring 192 has a rate defined as the change in the force it exerts, divided by the change in deflection of the spring. The spring is compressible and has a spring force that is defined by the product of the spring rate or constant (k) and the spring displacement (x). In one or more embodiments, the spring 192 has a rate that provides a compression force within the spring 192 that can increase to cause the first pulsing element 126 and the second pulsing element 136 to disengage or to cause the second pulsing element 136 to move distally past the first pulsing element 126, without rotation of the plunger rod. In one or more embodiments, the spring has a rate controls the pressure of the flush solution to an amount below about 25 psi. In one or more alternative embodiments, the spring has a rate that controls the pressure of the flush solution to an amount below about 20 psi. In one or more embodiments, the spring 192 has a rate such that the disengagement of the first pulsing element 126 and the second pulsing that causes the spring 192 to expand and the compression force to decrease.

In one or more alternative embodiments, the pulse control element 190 may be provided as a lever arm (not shown) that includes a first end disposed adjacent to or attached to the thumb press body 173 and the second end disposed adjacent to the proximal end of the plunger rod. The lever arm may be made of metal or plastic. The lever arm may include a first lever arm and a second lever arm that form an acute angle. In such embodiments, the application of a force in the distal direction on the thumb press 170 and the plunger rod 130 would compress the first lever arm and the second lever arm and such compression would provide within the lever arm that can increase to cause the first pulsing element 126 and the second pulsing element 136 to disengage or to cause the second pulsing element 136 to move distally past the first pulsing element 126, without rotation of the plunger rod.

Movement of the thumb press 170 relative to the plunger rod 130 causes the pulse control element 190 or the spring 192 to expand and compress. Specifically, when a force is applied to the thumb press 170 in the distal direction, the thumb press moves in the distal direction relative to the plunger rod and the tabs 180 of the thumb press 170 move from the proximal end 156 of the openings 154 of the proximal attachment portion 150 to the distal end 155 of the openings 154. The space within the hollow interior 153 of the proximal attachment portion 150 and the recessed portion 177 of the plunger-engaging portion 174 decreases and the thumb press 170 exerts a force on the spring 192 in the distal direction. The closed distal end 151 of the proximal attachment portion 150 prevents movement or expansion of the spring 192 and, therefore, the spring is compressed as more clearly shown in FIG. 10. Moreover, the application of a force in the proximal direction on the plunger rod 130 or the thumb press 170 will cause the tabs 180 to move in the proximal direction until they are in contact with the proximal end 156 of the openings of the proximal attachment portion. The second annular disc 175 of the thumb press 170 prevents the spring from moving or expanding and, therefore, the spring 192 compresses. Release of the distally directed force on the thumb press or the proximally directed force on the plunger rod allows the spring 192 to expand to its original relaxed state.

Figure 9:
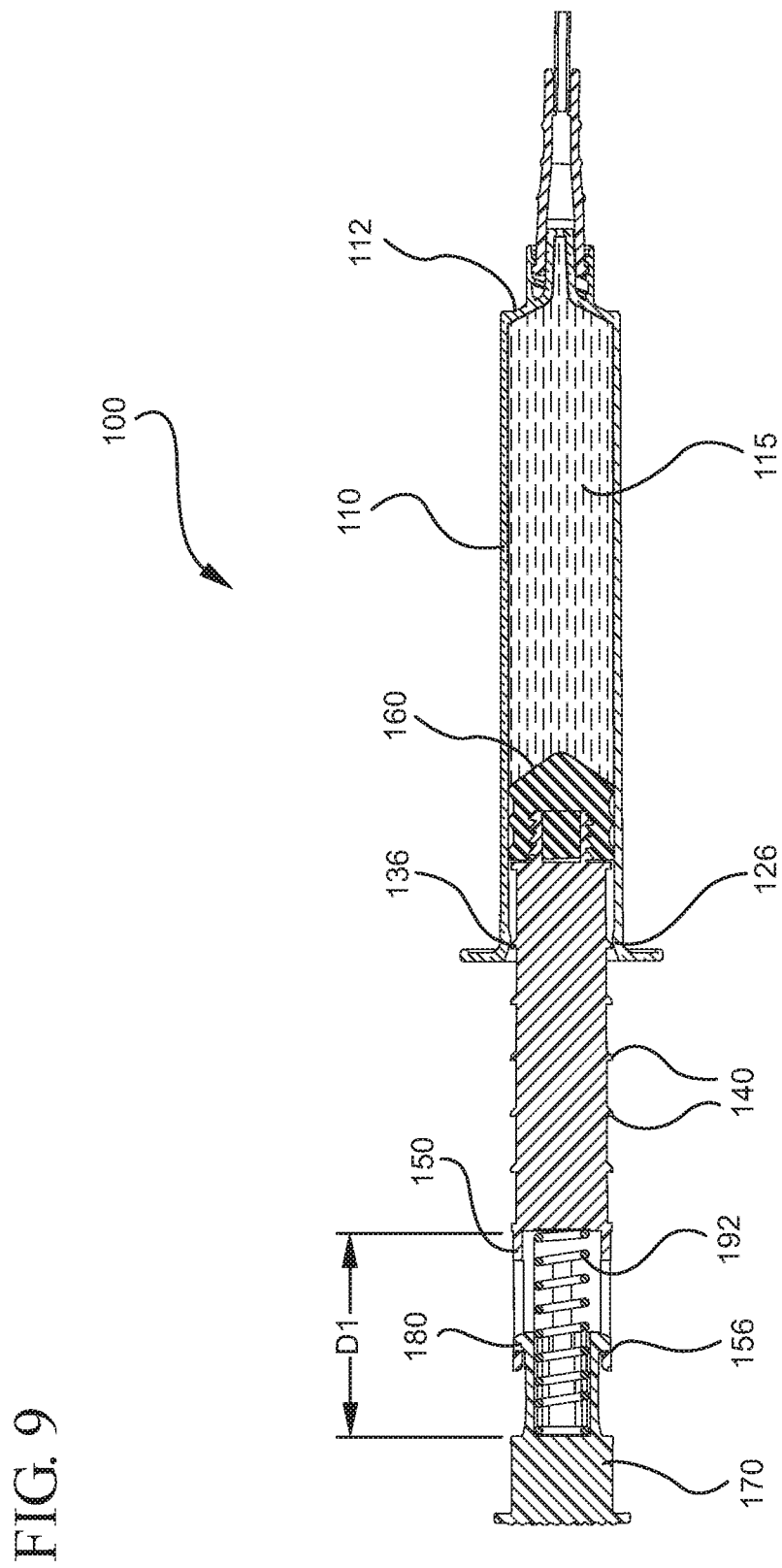
FIG. 9 illustrates flush syringe assembly shown in FIG. 4 attached to a catheter connector.

To use the flush syringe assembly described herein to remove debris from a catheter or, in other words, to expel flush solution having pulsing flow into a catheter, the plunger rod 130 and stopper 160 are assembled and inserted into the syringe barrel 110 with a chamber 115 that is filled with the desired amount of flush solution, as shown in FIG. 9. The stopper 160 forms a fluid tight seal with the interior surface 114 of the syringe barrel 110. The spring 192 is positioned between the thumb press 170 and the plunger rod 130 in an uncompressed or expanded state with a length of D1. The engagement tabs 180 are positioned at the distal end 155 of the openings 154 of the proximal attachment portion 150 of the plunger rod.

The movement of the plunger rod 130 within the syringe barrel 110 creates an interference force. The second pulsing element 136 of the plunger rod is aligned to interact or engage with the first pulsing element 126 of the syringe barrel to create an engagement force. In this configuration, the engagement force between the first pulsing element 126 and the second pulsing element 136 provide variations in the interference force between the plunger rod and the syringe barrel, which causes pulsatile movement of the plunger rod 130 as it moves in the at least the distal direction within the syringe barrel 110. The engagement force between the first pulsing element 126 and the second pulsing element 136 may be described as a proximally directed force on the plunger rod. In other words, the engagement force resists the distally directed force applied to the plunger rod. The engagement force may enhance or facilitate compression of the pulse control element 190.

Figure 10:
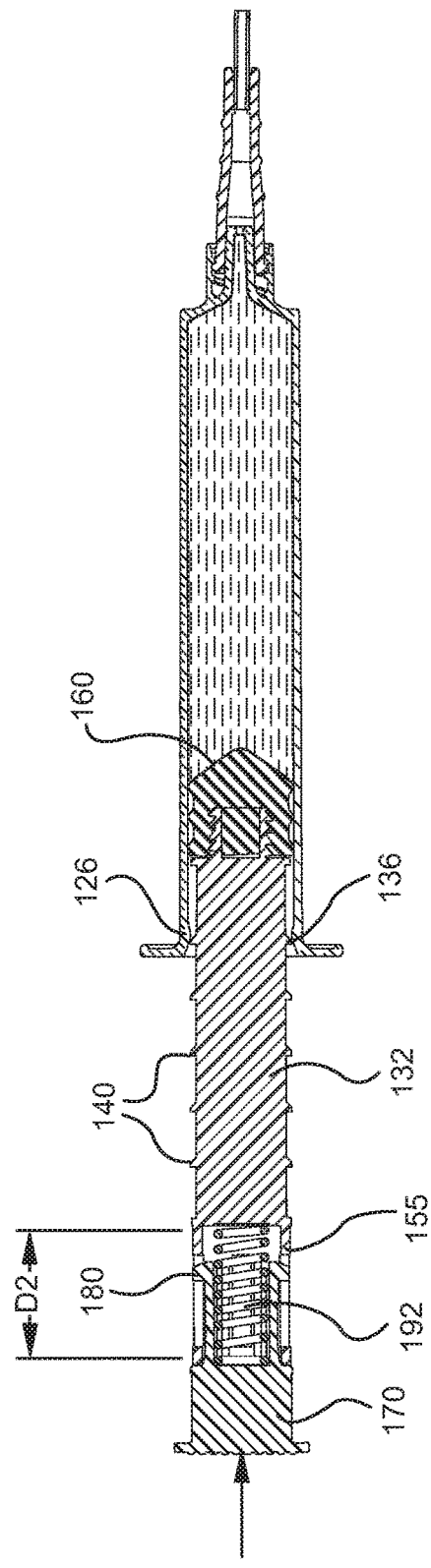
FIG. 10 shows the flush syringe assembly of 9 after application of an initial force on the plunger rod in the distal direction and engagement of a first pulsing element disposed on the barrel and a second pulsing element disposed on the plunger rod.
Figure 10A:
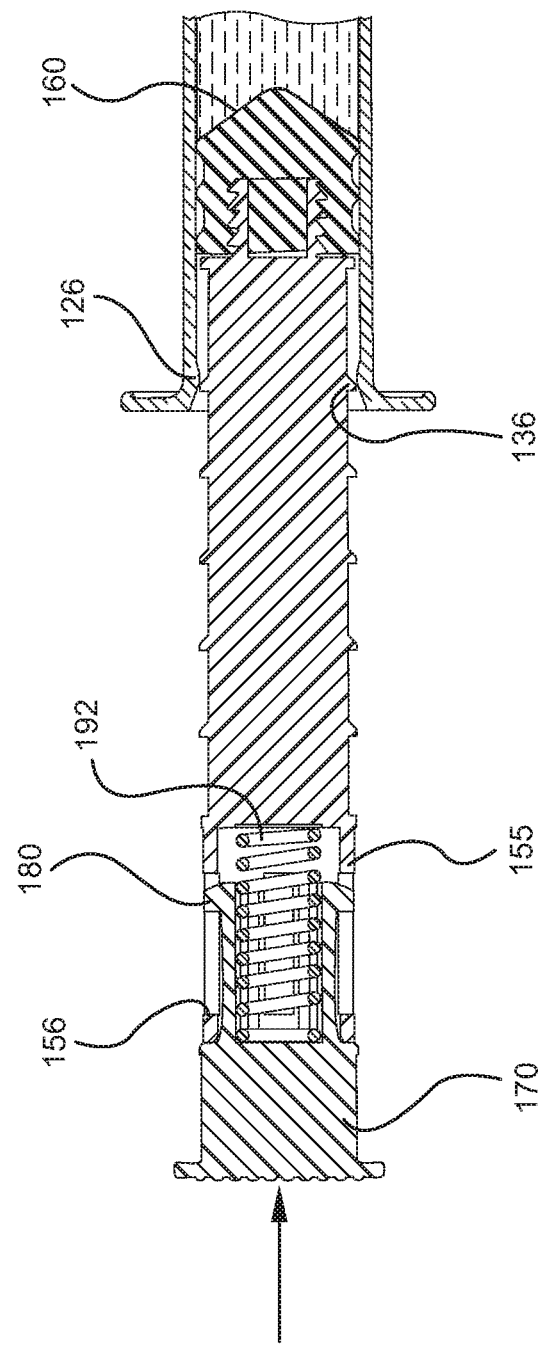
FIG. 10A illustrates a enlarged partial view of the flush syringe assembly shown in FIG. 10.

FIG. 10 illustrates the initial interaction between the first pulsing element 126 and the second pulsing element 136 as a force is applied to the plunger rod 130 in the distal direction, the interaction or engagement between the first pulsing element 126 and the second pulsing element 136 creates or provides the engagement force and provides resistance to movement of the plunger rod in the distal direction. As the user continues to apply a force on the thumb press 170 and the plunger rod 130 in the distal direction, the engagement tabs 180 move in the distal direction relative to the plunger rod and the proximal attachment portion 150 until the engagement tabs 180 are adjacent to the distal end 155 of the openings 154.

In known flush syringe assemblies, the user would have to apply a greater force in the distal direction to overcome the engagement force. Moreover, the flow of the flush solution would be stopped abruptly requiring even more force being exerted by the user to overcome the engagement force. There is often no control over the amount of additional force that is applied in the distal direction to overcome the engagement force. This leads to excessive force being applied to the plunger rod that causes the flush solution have excessive fluid pressure that can lead to overpressurization of the catheter and could lead to vein blowout. The user would have no way sensing that the pressure in the catheter has reached such high levels.

Figure 11:
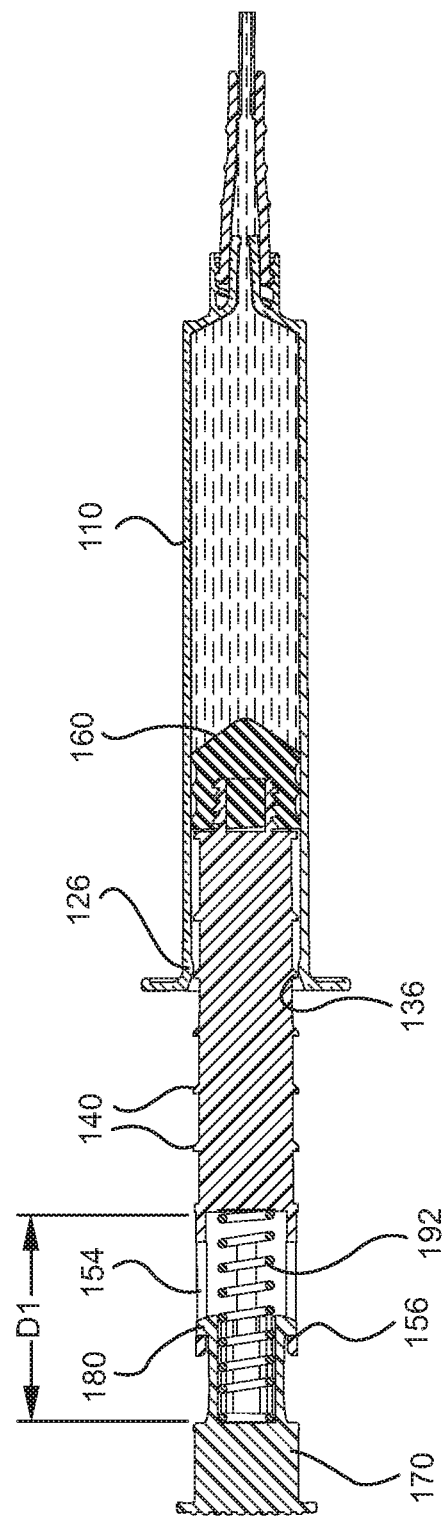
FIG. 11 illustrates the flush syringe assembly of FIG. 10 after the first pulsing element of the syringe barrel disengages from the second pulsing element of the plunge rod.

In the embodiment shown, the pulse control element 190 is disposed between the thumb press 170 and the plunger rod 130 is compressed by the resistance caused by the engagement force between the first pulsing element 126 and the second pulsing element 136 and the continued application of a distally directed force by the user on the thumb press 170 and the plunger rod 130. The user would not detect any substantial change in the force required to expel the flush solution due to the compression of the spring 192. The compression of the spring 192 creates a compression force that increases as the spring is further compressed. Initially, as the user applies a distally directed force on the plunger rod 130 and the thumb press 170, the engagement force between the first pulsing element 126 and the second pulsing element 136 is low or non-existent. At this time, the compression of the spring 192 remains low and the compression force is not greater than the engagement force between the first pulsing element 126 and the second pulsing element 136. As the user continues to apply a distally directed force on the thumb press 170 and the plunger rod 130, the spring further compresses until the spring 192 has a length of D2. The compression force of the spring increases until it is greater than the engagement force between the first pulsing element 126 and the second pulsing element 136, as shown in FIGS. 10 and 11. The second pulsing element 136 of the plunger rod disengages from the first pulsing element 126 and moves distally past the first pulsing element 126, as shown in FIG. 11. The disengagement of the first pulsing element 126 and the second pulsing element 136 and the movement of the plunger rod impart pulsing flow to the flush solution. At this time, the engagement force decreases or is no longer present. The length of the spring 192 expands to D1. The disengagement of the first pulsing element 126 and the second pulsing element 136 and the movement of the plunger rod allow the spring to expand and the compression force of the spring 192 is decreased. The removal of the engagement force and the expansion of the spring 192 cause the plunger rod to expand or the thumb press 170 to move in the proximal direction relatively to the plunger rod and the engagement tabs 180 move toward the proximal end 156 of the openings 154 of the proximal attachment portion 150 of the plunger rod.

Figure 12:
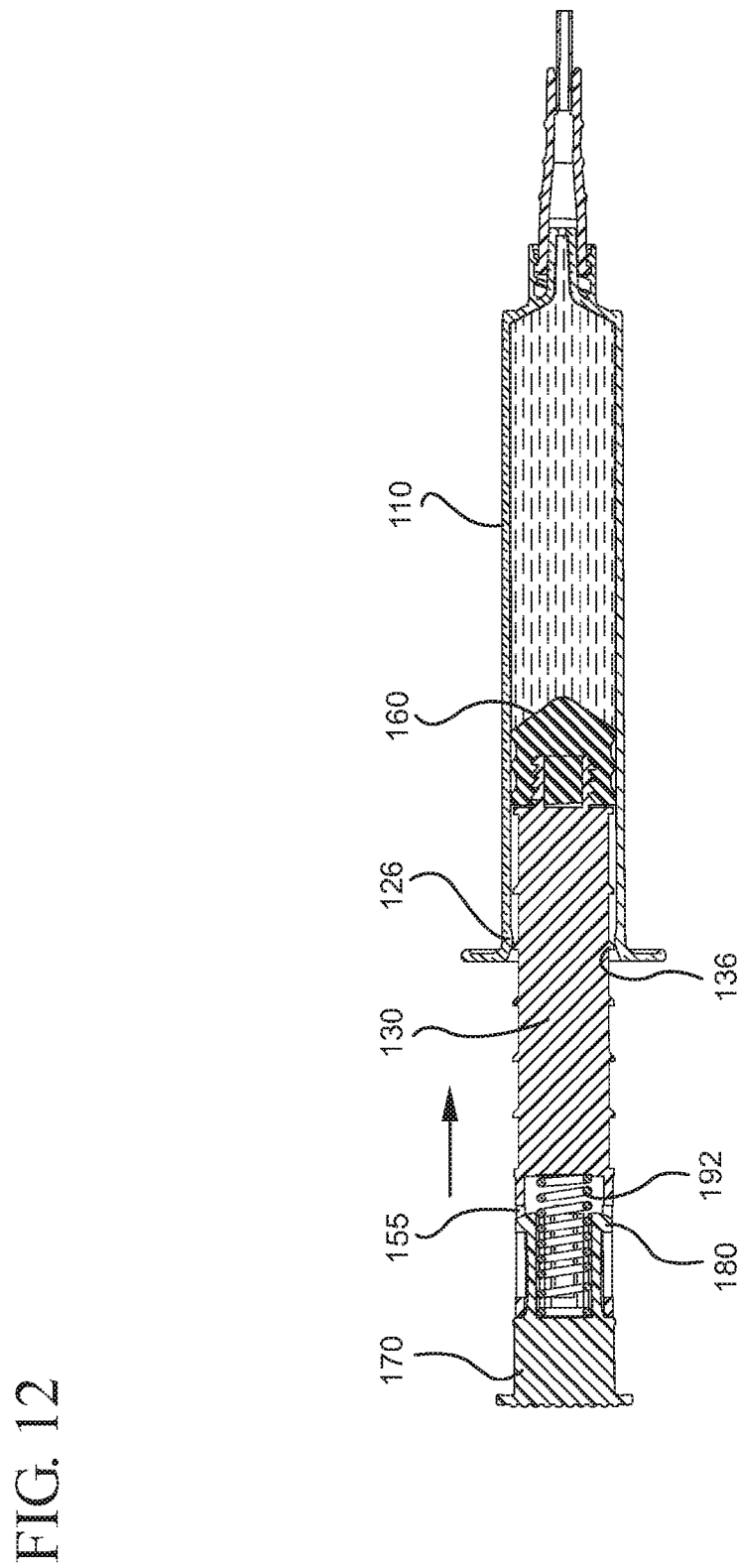
FIG. 12 shows the flush syringe assembly of FIG. 11 after application of a continued force on the thumb press and plunger rod in the distal direction and further engagement of the first pulsing element of the barrel and the second pulsing element of the plunger rod.
Figure 13:
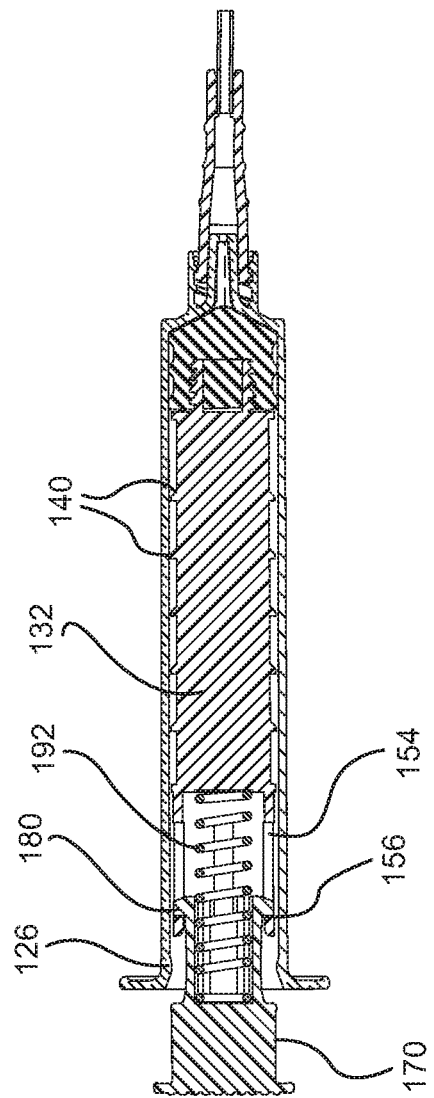
FIG. 13 illustrates the flush syringe assembly of FIG. 12 after the contents of the syringe barrel have been expelled upon continuous application of force on the thumb press and the plunger rod in the distal direction.
Figure 14:
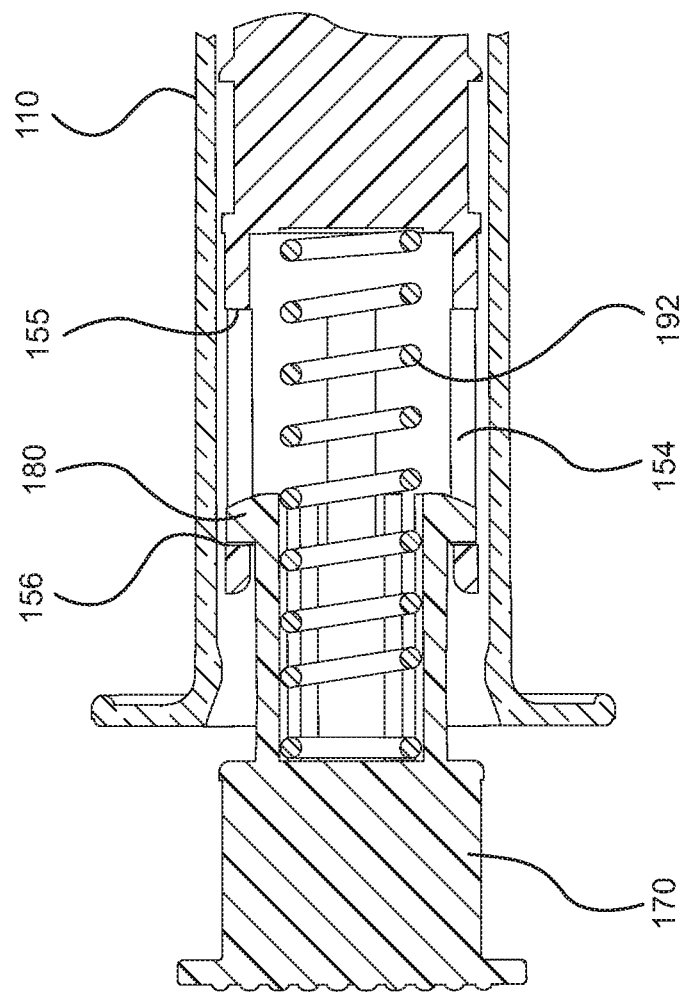
FIG. 14 illustrates a enlarged partial view of the pulse control element of the flush syringe assembly of FIG. 13.

As shown in FIGS. 12-14, as the user continues to apply a distally directed force on the thumb press 170 and the plunger rod 130 to expel the flush solution, the first pulsing element 126 and the second pulsing element 136 continue to engage and disengage. As the first pulsing element 126 and the second pulsing element 136 engage and disengage, the spring 192 compresses and expands such that the engagement force and the compression force increase and decrease relative to one another to allow the plunger rod to expel the flush solution having pulsing flow from the syringe barrel. The compression force of the spring 192 prevents the user from actively applying excessive force to the plunger rod 130 and thumb press 170 to overcome the engagement force between the first pulsing element 126 and the second pulsing element 136 and prevent overpressurization of the catheter. After all of the flush solution is expelled from the syringe barrel 110, the spring 192 is positioned in an expanded state with a length of D1, as shown in FIGS. 13 and 14.

Figure 15:
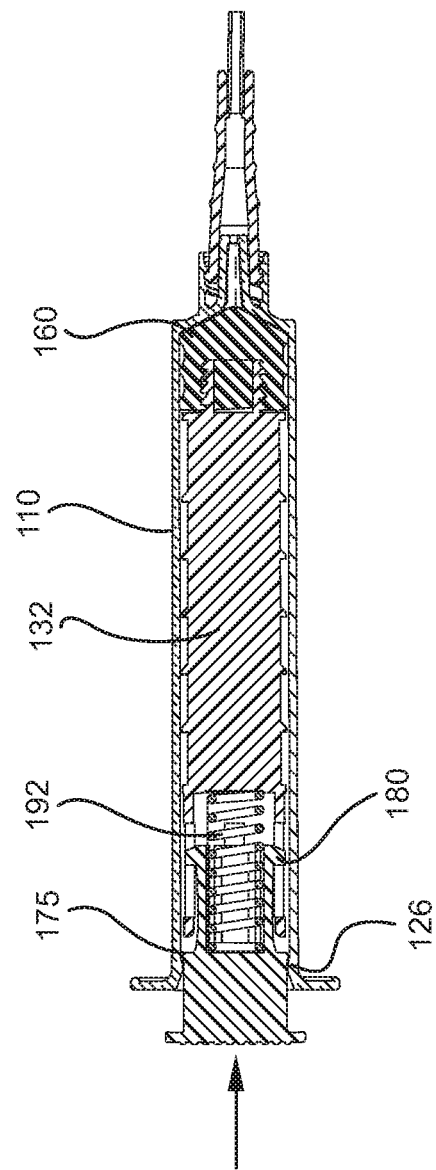
FIG. 15 shows the flush syringe assembly of FIG. 13 after application of a locking force in the distal direction to lock the thumb press with the syringe barrel.
Figure 16:
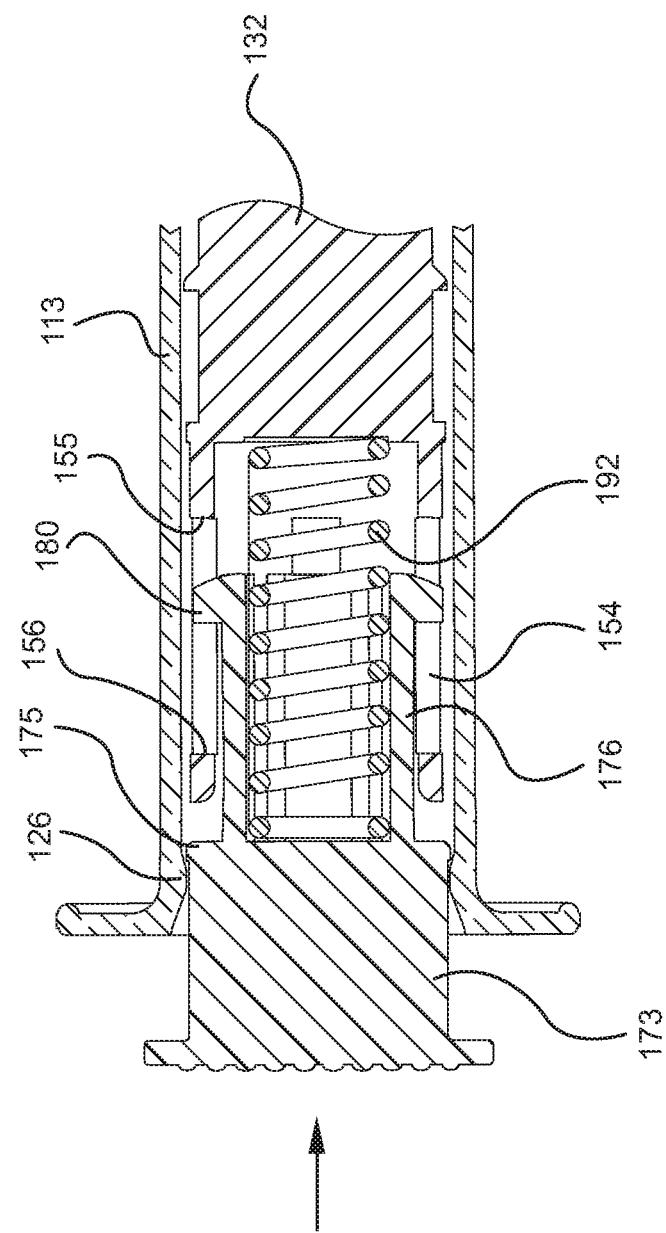
FIG. 16 illustrates a enlarged partial view of the pulse control element of the flush syringe assembly of FIG. 15.

In one embodiment, the flush syringe assembly 100 includes structure for preventing reflux, which minimizes the use of heparin to lock catheters or the need for positive displacement valves. Typically, to prevent reflux, the user is encouraged to maintain a positive pressure in the line during the flush procedure to prevent reflux or compression of the stopper that can draw blood back into the catheter, where it can clot and seal the catheter. The compression of the spring 192 by application of a distally directed force on the thumb press 170 and the plunger rod 130 after the stopper 160 is in contact with the distal wall 112 of the syringe barrel, as shown in FIGS. 15 and 16, applies positive pressure and prevents reflux. The user may also maintain such positive pressure by applying a sufficient force in the distal direction to the thumb press 170 or continuing to apply a distally directed force to the thumb press to lock the thumb press 170 into the barrel. Specifically, as shown in FIG. 15-16, the application of sufficient force to the thumb press 170 causes the second annular disc 175 to engage the first pulsing element 126 or the retaining ring 127 of the barrel. Thereafter, the retaining ring 127 continues to apply a distally directed force on the thumb press 170 and the spring 192 remains compressed and exerts a compression force on the plunger rod 130 and stopper 160 in the distal direction.

Figure 17:
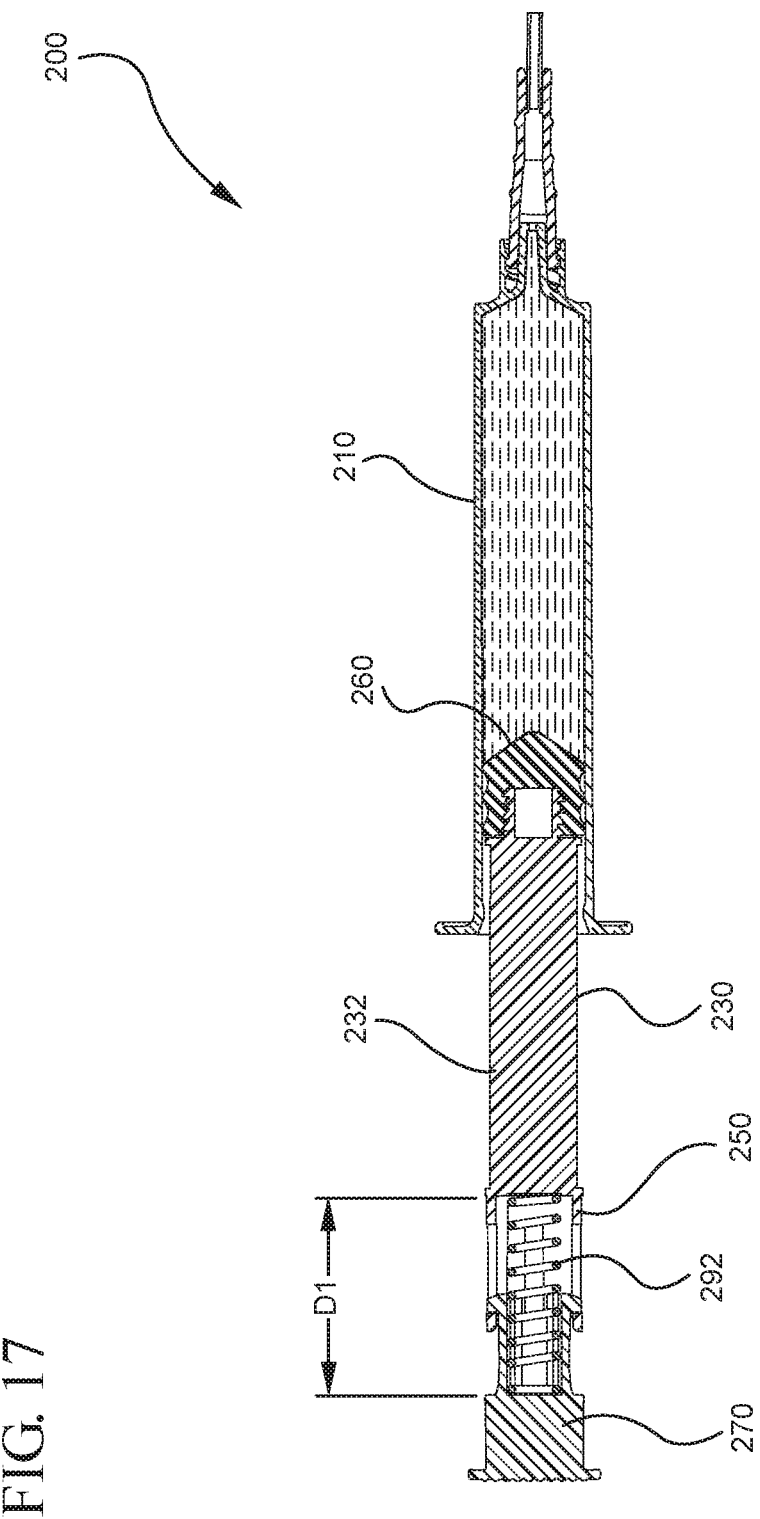
FIG. 17 shows a flush syringe assembly according to one or more embodiments in which the second pulsing element is positioned to not engage the first pulsing element.
Figure 18:
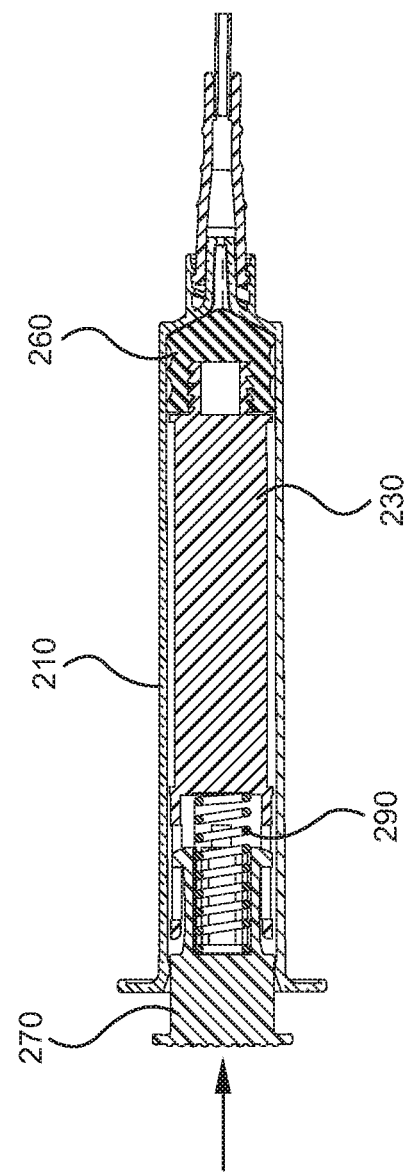
FIG. 18 shows the flush syringe assembly of FIG. 17 upon application of a force in the distal direction to expel the contents of the syringe barrel have been expelled and upon application of a locking force in the distal direction to lock the thumb press with the syringe barrel.

An alternative embodiment of the flush syringe assembly 200 is shown in FIGS. 17-18. Specifically, the flush syringe assembly 200 permits the user to select whether to utilize pulsating flow or continuous flow to flush a syringe. As discussed above, the syringe barrel 110 and/or plunger rod 130 includes a first pulse element 126 and a second pulse element 136 that are positioned, shaped or disposed thereon in a manner that allows the user to select whether or not the first pulsing element 126 and the second pulsing element 136 engage and cause pulsatile movement. For example, if continuous and unimpeded movement of the plunger rod is desired, instead of the pulsatile movement, the user may rotate the plunger rod 130, barrel 110 or the retaining ring so that the first pulsing element 126 and the second pulsing element 136 are not aligned. As shown in FIG. 17, the flush syringe assembly 200 includes a syringe barrel 210 with a first pulsing element 226 and the plunger rod 230 with a plunger rod body 232 a second pulsing element 236 (not shown) that is disposed on the plunger rod body 232 in such a manner that the plunger rod 230 may be rotated within the syringe barrel 210 to prevent engagement or interaction with the first pulsing element 226. The flush syringe assembly 200 also includes a thumb press 270 attached the plunger rod by a proximal attachment portion 250. As the user applies a distally directed force on the thumb press and the plunger rod 230, the lack of interaction or engagement between the first pulsing element 226 and the second pulsing element 236 causes the plunger rod 230 to move within the syringe barrel in a continuous and uninterrupted manner. Specifically, the interaction force between the plunger rod 230 and the syringe barrel 210 remains constant and without the variations that are caused by pulsatile movement of the plunger rod. As the flush solution is expelled, as shown in FIG. 18, the user may continue to apply a force on the thumb press in the distal direction such that the second annular disc to engage the first pulsing element 226. The pulse control element 290 disposed within the thumb press 270 and the proximal attachment portion 250 is compressed and continues to exert the compression force to the plunger rod 230 and stopper 260 in the distal direction.

The flush syringe assemblies described herein may also include visual or other indication elements to indicate the position of the first and second pulsing elements with respect to each other and thus, indicate whether movement of the plunger rod within the barrel will be pulsatile or continuous and unimpeded. For example, the thumb press may have a color disposed on a portion of the thereon that is aligned with the second pulsing element disposed on the plunger rod, as described herein. The barrel may include corresponding color disposed on the finger flange or other portion of the barrel that is aligned with the first pulsing element disposed on the barrel. Accordingly, in use the alignment of the colored portions on the thumb press and the barrel indicates to the user that the flush syringe assembly is configured for pulsatile movement of the plunger rod within the barrel. Other visual markers may also be utilized, for example, symbols and words may be disposed on the thumb press and barrel.

A second aspect of the present invention pertains to a method for flushing a catheter. In one or more embodiments, the method includes attaching a flush syringe assembly as described herein to a catheter. The flush syringe assembly may be filled or pre-filled with the desired amount of flush solution. The method includes applying a continuous force in the distal direction to the plunger rod to create sufficient compression force within the spring until it overcomes the engagement force between the first pulsing element and the second pulsing element. In one or more embodiments, the method further includes continuing to apply the force in the distal direction on the thumb press 170 and the plunger rod 130 until the thumb press 170 and/or plunger rod 130 is locked within the syringe barrel when the stopper is in contact with the distal wall of the syringe barrel.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed:

1. A flush syringe assembly comprising:
    a barrel including a side wall having an inside surface defining a chamber for retaining fluid, an open proximal end and a distal end including a distal wall with a tip extending distally therefrom and having a passageway therethrough in fluid communication with the chamber, the barrel comprising a first pulsing element on the inside surface of the barrel;
    a plunger rod disposed within the barrel, the plunger rod comprising a distal end, a proximal end, a plunger rod body extending from the distal end to the proximal end and having a second pulsing element;
    a thumb press slidably attached to the proximal end of the plunger rod;
    a pulse control element disposed between the thumb press and the proximal end of the plunger rod; and
    a stopper disposed at the distal end of the plunger rod to form a fluid-tight seal with the inside surface of the barrel,
    wherein in a first position, the second pulsing element engages the first pulsing element to provide an engagement force that resists distally directed force applied to the plunger rod, and force applied to the thumb press in the distal direction exceeds the engagement force to cause pulsatile movement of the plunger rod as it moves within the barrel in the distal direction; and in a second position, upon rotation of the plunger rod to prevent the second pulsing element from engaging with the first pulsing element, there is continuous movement of the plunger rod as it moves within the barrel in the distal direction.

2. The flush syringe assembly of claim 1, wherein the pulse control element comprises a spring that compresses to provide a compression force upon application of a distally directed force on the thumb press and expands as the distally directed force is released.

3. The flush syringe assembly of claim 2, wherein the spring has a spring rate so that application of a continuous distally directed force on the thumb press in the first position increases the compression force until it is greater than the engagement force and causes the first pulsing element to disengage from the second pulsing element permitting the plunger rod to move in a distal direction.

4. The flush syringe assembly of claim 3, wherein the spring rate is such that the disengagement of the first pulsing element and the second pulsing element in the first position causes the spring to expand and the compression force to decrease.

5. The flush syringe assembly of claim 2, wherein the thumb press further comprises a proximal end, a distal end, a plurality of engagement tabs disposed at the distal end of the thumb press, and the plunger rod further comprises a plurality of openings having a distal end, a proximal end and a length between the distal end and the proximal for receiving the engaging tabs, the engagement tabs configured to slide along the length of the plurality of openings as the compression force is applied to the thumb press in the distal direction and the compression force is released in the first position.

6. The flush syringe assembly of claim 1, wherein the thumb press comprises a locking element that engages with the first pulsing element in the first position to lock the thumb press at least partially within the barrel when the stopper is in contact with the distal wall of the barrel and causes the pulse control element to exert a force on the plunger rod in a distal direction.

7. The flush syringe assembly of claim 1, wherein the first pulsing element comprises a retaining ring that extends inwardly into the chamber of the barrel.

8. The flush syringe assembly of claim 1, wherein the second pulsing element comprises a distally facing ramped surface.

9. The flush syringe assembly of claim 8, wherein the second pulsing element further comprises a proximally facing perpendicular face.

10. The flush syringe assembly of claim 9, wherein the proximally facing perpendicular face engages the first pulsing element to prevent proximal movement of the plunger rod within the barrel.

11. The flush syringe assembly of claim 8, wherein the plurality of projections are disposed at regular intervals along the plunger rod body.

12. The flush syringe assembly of claim 1, wherein the plunger rod has a plurality of projections disposed along the plunger rod body.

13. The flush syringe assembly of claim 1 further comprising a visual indicator to indicate whether the assembly is in the first position or the second position.

14. The flush syringe assembly of claim 13, wherein the visual indicator includes one or more of: color, symbols, and words.

15. A flush syringe assembly comprising:
a barrel including a side wall having an inside surface defining a chamber for retaining fluid, an open proximal end and a distal end including a distal wall with a tip extending distally therefrom having a passageway therethrough in fluid communication with the chamber, the open proximal end of the barrel comprising at least one protrusion extending inwardly into the chamber adjacent the open proximal end;
a plunger rod disposed within the barrel comprising a compressible plunger rod body with a distal end and a proximal end, and a plurality of projections disposed along the plunger rod body, each projection having a distally facing ramped surface and a proximally facing perpendicular surface so that in a first position, a distally directed force to a thumb press causes engagement of the distally facing ramped surface with the protrusion on the barrel to provide an interference force with variations and cause pulsatile movement of the plunger rod as it moves within the barrel in the distal direction and imparts pulsing flow to a solution in the chamber, the plunger rod body further comprising a hollow portion including a spring having a rate so that the spring is initially compressed to provide a force that is less than the interference force and upon further application of distally directed force to the thumb press, the spring is compressed to provide force greater than the interference force; and in a second position, upon rotation of the plunger rod, a distally directed force to the thumb press causes a continuous movement of the plunger rod as it moves within the barrel in the distal direction; and
a stopper disposed at the distal end of the plunger rod for forming a fluid-tight seal with the inside surface of the barrel.

16. The flush syringe assembly of claim 15, wherein the compressible plunger rod body comprises a telescoping segment attached to the proximal end of the plunger rod, the telescoping segment configured to slide in and out of the plunger rod body to reduce and increase the length of the plunger rod body.

17. The flush syringe assembly of claim 16, wherein the spring is disposed between the telescoping segment and the plunger rod body that compresses and generates a compression force as a force is applied to the plunger rod in the distal direction and expands as the compression force is released.

18. The flush syringe assembly of claim 17, wherein an expansion of the spring causes the telescoping segment to slide out of the plunger rod body to increase the length of the plunger rod body and the compression of the spring allows the telescoping segment to slide into the plunger rod body to reduce the length of the plunger rod body.

19. The flush syringe assembly of claim 15, wherein the interaction of the proximally facing perpendicular surface with the protrusion of the barrel prevents movement of the plunger rod in a proximal direction in the second position.

20. The flush syringe assembly of claim 15, wherein the plunger rod comprises a locking element that engages with the protrusion of the barrel to lock at least a portion of the plunger rod within the barrel when the stopper is in contact with the distal wall of the barrel and causes the spring to exert a force on the plunger rod in a distal direction.

* * * * *

UNITED STATES PATENT AND TRADEMARK OFFICE
CERTIFICATE OF CORRECTION

PATENT NO. : 10,463,798 B2
APPLICATION NO. : 15/864185
DATED : November 5, 2019
INVENTOR(S) : Anthony J. Kosinski et al.

It is certified that error appears in the above-identified patent and that said Letters Patent is hereby corrected as shown below:

On the Title Page

Page 2, Item (56), Column 2, under "References Cited U.S. PATENT DOCUMENTS", Line 33, insert --D461243, 08/2002, Niedospial et al--.

Signed and Sealed this
Twenty-third Day of June, 2020

Andrei Iancu
*Director of the United States Patent and Trademark Office*